US010436715B2

(12) United States Patent
Tada

(10) Patent No.: US 10,436,715 B2
(45) Date of Patent: Oct. 8, 2019

(54) FLUORESCENCE READING DEVICE

(71) Applicant: FUJIFILM Corporation, Tokyo (JP)

(72) Inventor: Takuji Tada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/112,048

(22) Filed: Aug. 24, 2018

(65) Prior Publication Data

US 2019/0064069 A1   Feb. 28, 2019

(30) Foreign Application Priority Data

Aug. 25, 2017   (JP) .................................. 2017-162487

(51) Int. Cl.
   *G01N 21/64* (2006.01)
   *G02B 3/00* (2006.01)
   (Continued)

(52) U.S. Cl.
   CPC ....... *G01N 21/6456* (2013.01); *G01N 21/645* (2013.01); *G01N 21/76* (2013.01); *G02B 3/005* (2013.01); *G02B 3/0056* (2013.01); *G02B 3/0062* (2013.01); *G02B 3/0075* (2013.01); *G02B 3/06* (2013.01); *G02B 26/0875* (2013.01);
   (Continued)

(58) Field of Classification Search
   CPC ............... G01N 21/6456; G01N 21/76; G01N 2021/6484; G01N 2021/6478; G02B 26/0875; G02B 3/005; G02B 3/06; G02B 3/0062; G02B 3/0075; G02B 3/0056
   See application file for complete search history.

(56) References Cited

U.S. PATENT DOCUMENTS 6,366,338 B1 * 4/2002 Masubuchi ................ B41J 2/45
                                                        355/41
2006/0145100 A1   7/2006 Sorebo
(Continued)

FOREIGN PATENT DOCUMENTS

DE   102006036171 A1 * 1/2008   ................ B01L 7/52
EP   2533033 A1   12/2012
(Continued)

OTHER PUBLICATIONS

Partial European Search Report, dated Feb. 11, 2019, for European Application No. 18189965.9.
(Continued)

*Primary Examiner* — Kiho Kim
(74) *Attorney, Agent, or Firm* — Birch, Stewart, Kolasch & Birch, LLP

(57) ABSTRACT

Provided is a fluorescence reading device capable of narrowing a distance between a lens unit and an observation object to a distance according to a focal length of a refractive index distribution type lens and focusing fluorescence emitted from the observation object on detecting unit without blurring. Optical fiber sub-bundles equivalent to a light guide unit are buried in lens holding parts of a lens unit. Emission ends of the optical fiber sub-bundles are exposed to upper surfaces of the lens holding parts that face the observation object holding unit. The optical fiber sub-bundles guide the excitation light emitted from the light source and radiate the guided excitation light toward the surface of an observation object that faces the lens unit.

24 Claims, 25 Drawing Sheets

(51) Int. Cl.
*G02B 26/08* (2006.01)
*G02B 3/06* (2006.01)
*G01N 21/76* (2006.01)

(52) U.S. Cl.
CPC ........... *G01N 2021/6478* (2013.01); *G01N 2021/6484* (2013.01); *G01N 2201/0826* (2013.01)

(56) References Cited

U.S. PATENT DOCUMENTS

| | | |
|---|---|---|
| 2010/0208497 A1 | 8/2010 | Song et al. |
| 2014/0169734 A1* | 6/2014 | Kachru .................. G02B 6/42 385/33 |
| 2017/0013212 A1 | 1/2017 | Tanaka et al. |

FOREIGN PATENT DOCUMENTS

| | | | | |
|---|---|---|---|---|
| JP | 63-154943 A | | 6/1988 | |
| JP | 11051900 A | * | 2/1999 | ....... G01N 27/44721 |
| JP | 2005181949 A | * | 7/2005 | |
| JP | 2017-20822 A | | 1/2017 | |
| WO | WO 2009/107041 A1 | | 9/2009 | |
| WO | WO 2016/179246 A1 | | 11/2016 | |

OTHER PUBLICATIONS

Extended European Search Report dated May 23, 2019, for corresponding European Patent Application No. 18189965.9.

* cited by examiner

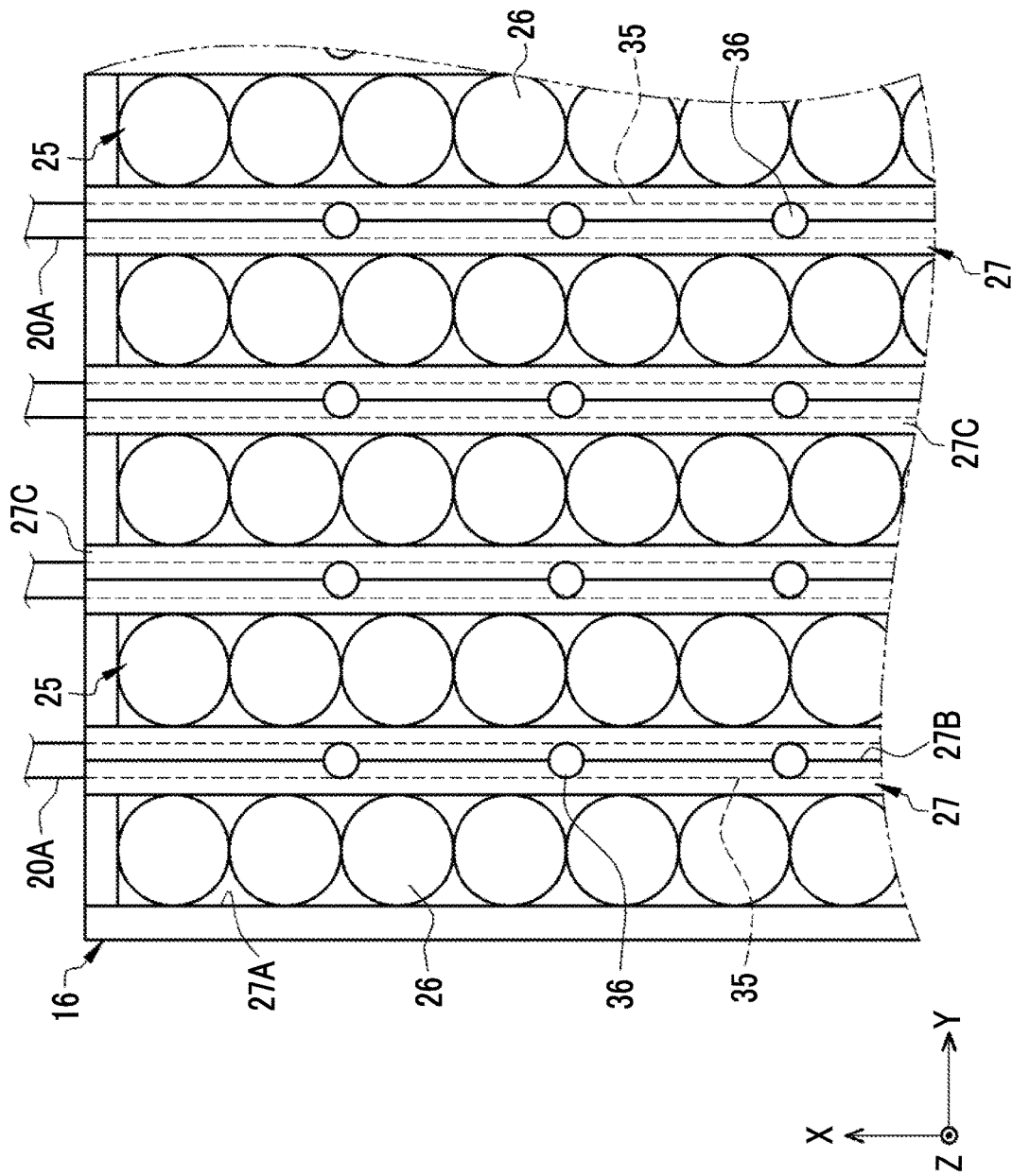

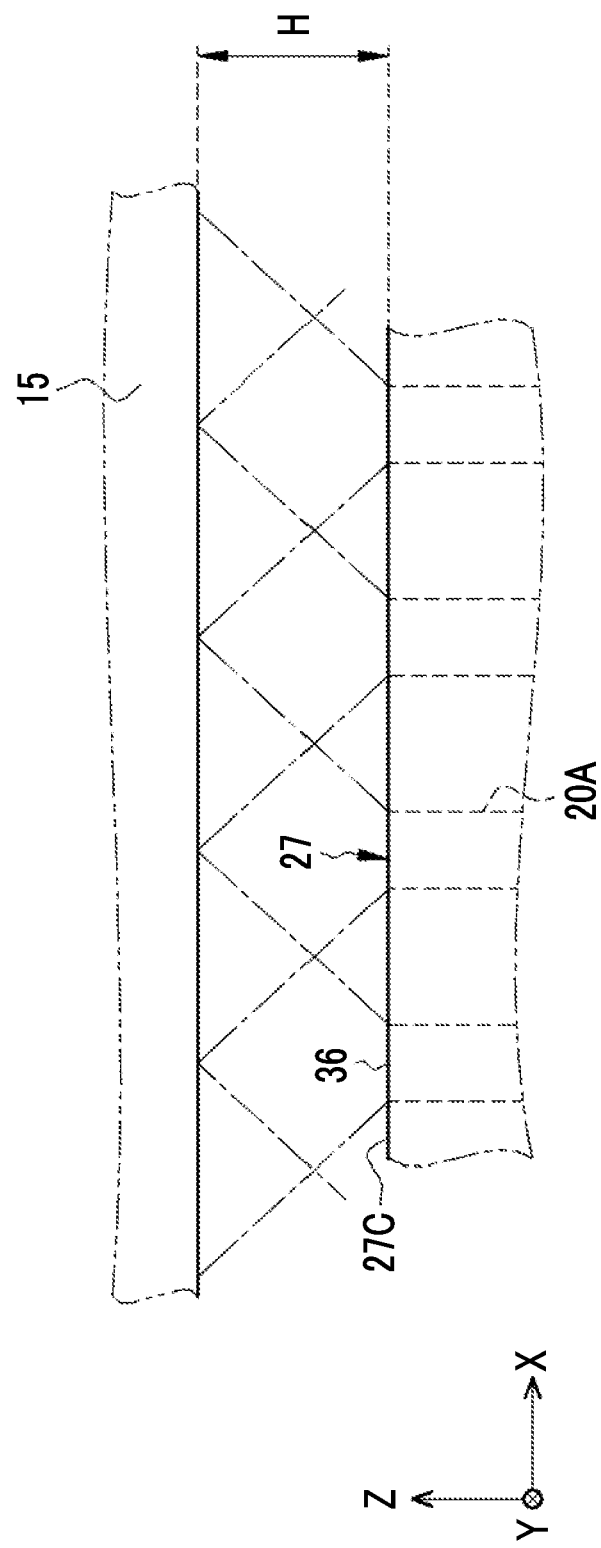

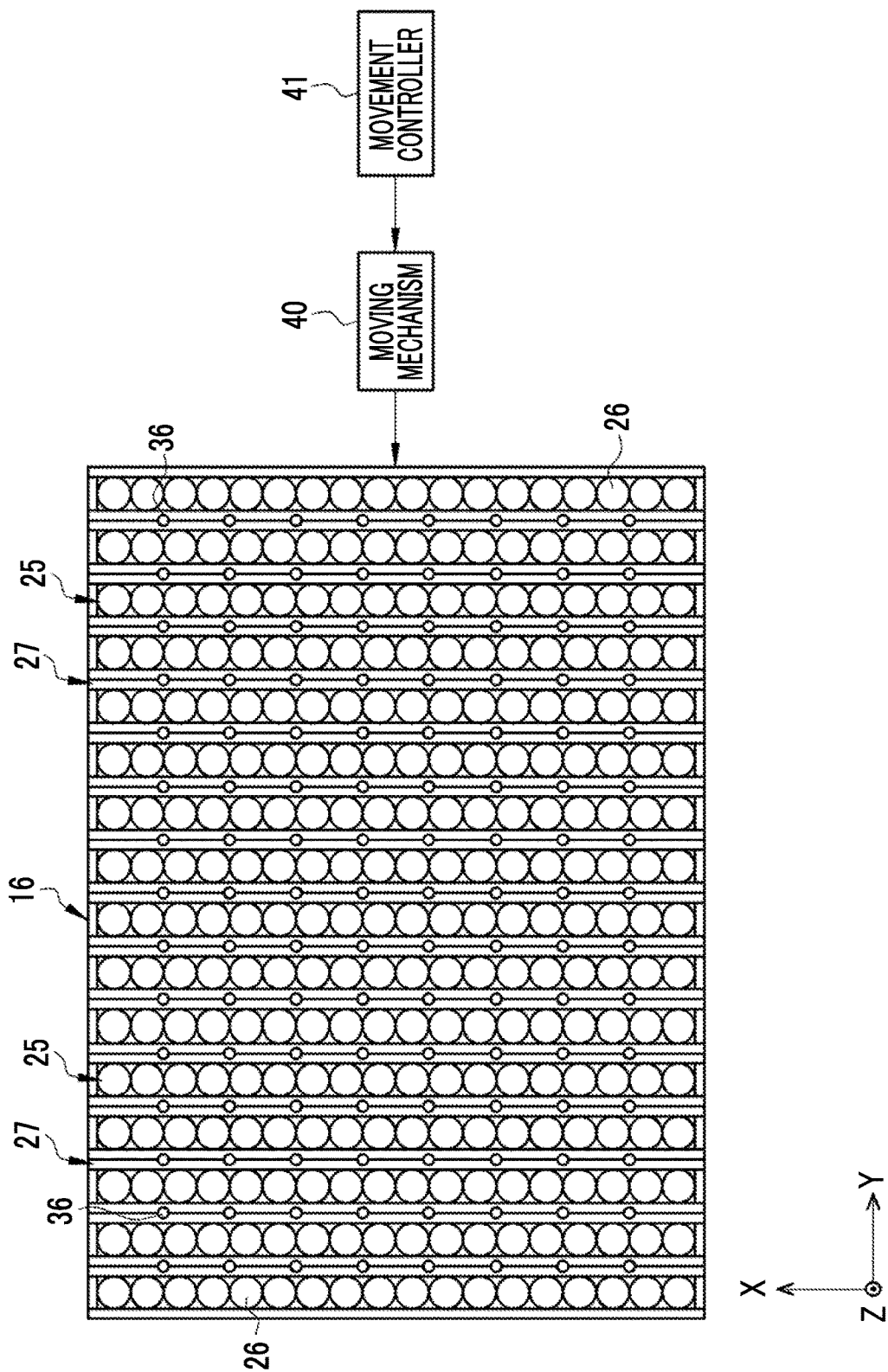

FIG. 18

| REFLECTIVITY, REFLECTED LIGHT QUANTITY, TRANSMITTED LIGHT QUANTITY OF INDIVIDUAL BEAM SPLITTERS AND TOTAL REFLECTION MIRROR IN CASE NUMBER OF REFLECTING MEMBERS (NUMBER OF SECOND LIGHT GUIDE PATHS) IS 10 | | | | ~90 |
|---|---|---|---|---|
| No. | REFLECTIVITY | REFLECTED LIGHT QUANTITY | TRANSMITTED LIGHT QUANTITY | |
| 1 | 10 | 10.00 | 90.00 | |
| 2 | 11.1 | 9.99 | 80.01 | |
| 3 | 12.5 | 10.00 | 70.01 | |
| 4 | 14.3 | 10.01 | 60.00 | |
| 5 | 16.7 | 10.02 | 49.98 | |
| 6 | 20 | 10.00 | 39.98 | |
| 7 | 25 | 10.00 | 29.99 | |
| 8 | 33.4 | 10.02 | 19.97 | |
| 9 | 50 | 9.99 | 9.99 | |
| 10 | 100 | 9.99 | 0.00 | |

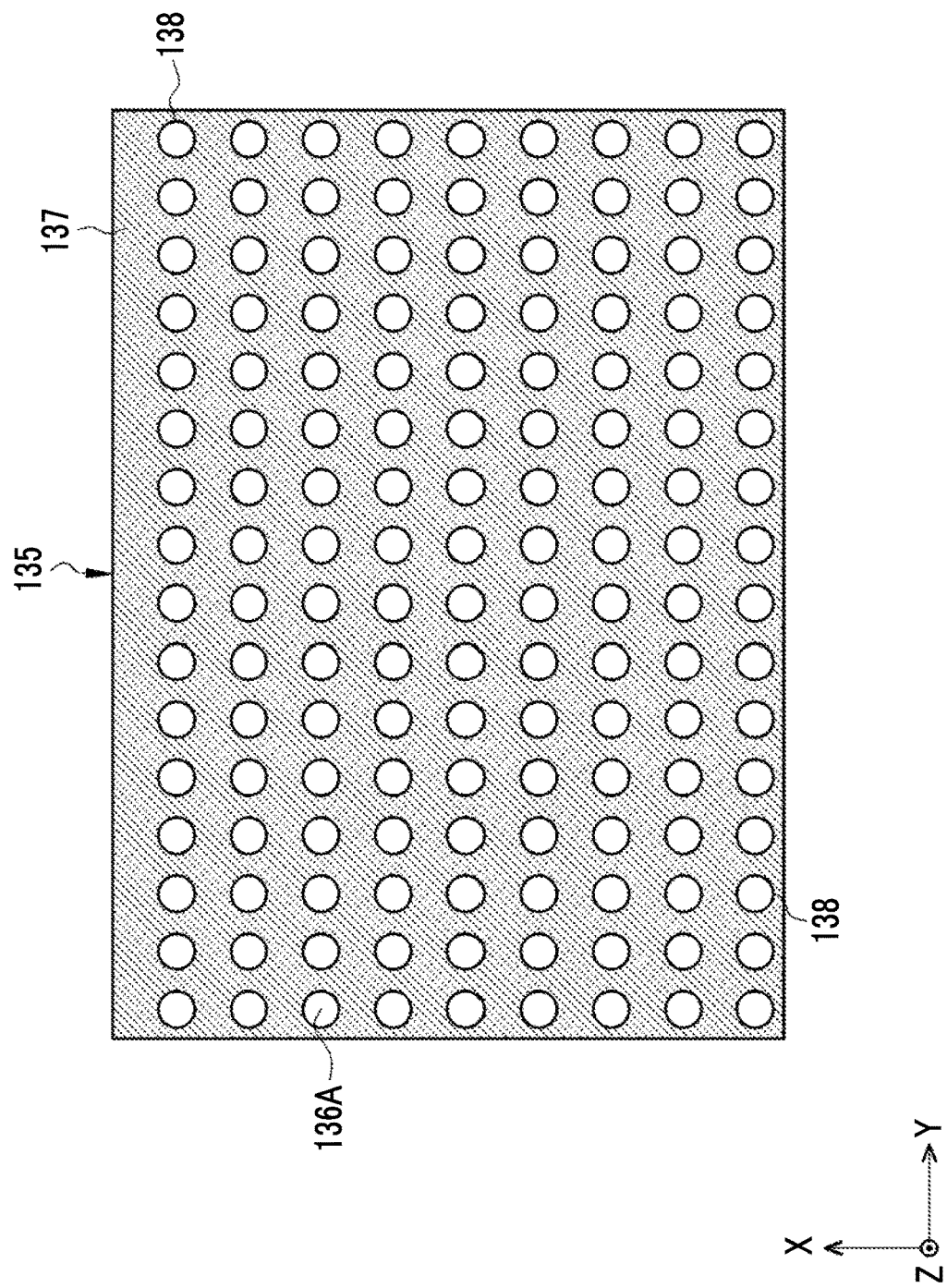

FLUORESCENCE READING DEVICE

CROSS-REFERENCE TO RELATED APPLICATION

This application claims priority under 35 USC 119 from Japanese Patent Application No. 2017-162487, filed 25 Aug. 2017, the disclosure of which is incorporated by reference herein.

BACKGROUND OF THE INVENTION

1. Field of the Invention

The present invention relates to a fluorescence reading device.

2. Description of the Related Art

In the related art, in the life science field, fluorescence reading devices, which detect fluorescence emitted from an observation object and generates and displays a fluorescence image according to this fluorescence, are widely used. For example, a fluorescence reading device described in JP2017-020822A (corresponding to US2017/013212A1) includes an observation object holding unit that holds an observation object, a light source that emits excitation light, a lens unit that focuses fluorescence emitted from the observation object on a detecting unit, and a detecting unit that detects the fluorescence focused by the lens unit.

In JP2017-020822A, the observation object holding unit is a parallel flat plate that transmits excitation light and fluorescence. The observation object is placed on the observation object holding unit. The lens unit and the detecting unit are disposed in this order below the observation object holding unit. That is, the lens unit is disposed between the observation object holding unit and the detecting unit.

The lens unit includes a plurality of lens arrays. In each lens array, a plurality of columnar refractive index distribution type lenses are arranged in a line in a first direction. The lens unit has a configuration in which the plurality of lens arrays are arranged in a second direction orthogonal to the first direction. That is, the lens unit has a configuration in which the plurality of refractive index distribution type lenses are two-dimensionally arranged. Moreover, the lens unit has a lens holding part. The lens holding part is constituted of a pair of parallel flat plates, extending in the first direction, having a fluorescence shielding property, and sandwiches and holds the lens arrays. In the detecting unit, detecting elements that detect the fluorescence are two-dimensionally arranged.

In an example illustrated in FIG. 11 of JP2017-020822A, the light source is disposed between the observation object holding unit and the lens unit, and more specifically, at an upper outer periphery of the lens unit, in other words, is disposed obliquely below the observation object holding unit. Since the light source equally radiates the excitation light to the entire surface of the observation object holding unit, a radiation surface of excitation light is directed to the observation object holding unit. For this reason, the excitation light is radiated toward the observation object obliquely from below the observation object holding unit. Additionally, the excitation light transmission filter, which transmits only the light within the preset wavelength range including the central wavelength of the excitation light, is integrally attached to the light source. A space for disposing the light source in which this excitation light transmission filter are integrated is provided between the observation object holding unit and the lens unit.

Since the excitation light is radiated toward the observation object obliquely from below the observation object holding unit, the excitation light is radiated to the surface of the observation object that is in contact with the observation object holding unit. Then, the fluorescence is emitted from the surface of the observation object that is irradiated with this excitation light and is in contact with the observation object holding unit. That is, in the observation object, the surface that is radiated with the excitation light and the surface from which the fluorescence is emitted is the same. For this reason, in JP2017-020822A, the light source is provided on the same side as the lens unit or the detecting unit.

SUMMARY OF THE INVENTION

Each refractive index distribution type lens has a relatively short focal length of, for example, 20 mm. For this reason, in a case where a distance between the lens unit and the observation object is not narrowed to a distance according to the focal length of each refractive index distribution type lens in the case of the lens unit using the refractive index distribution type lenses described in JP2017-020822A, an image focused on the detecting unit is blurred and the image quality of a fluorescence image deteriorates.

However, as in an example of FIG. 11 of JP2017-020822A, in a case where the light source is disposed between the observation object holding unit and the lens unit, a space for disposing the light source should be provided between the observation object holding unit and the lens unit. For this reason, there is a concern that the distance between the lens unit and the observation object cannot be narrowed to the distance according to the focal length of the refractive index distribution type lens, the image focused on the detecting unit is blurred, and the image quality of the fluorescence image deteriorates.

This is because, in JP2017-020822A, the light source with which the excitation light transmission filter is integrated is used. The light source with which the excitation light transmission filter is integrated has a size of about 30 mm. For this reason, the space of at least about 30 mm is required between the observation object holding unit and the lens unit. Meanwhile, since the focal length of the refractive index distribution type lens is about 20 mm, it is physically impossible to narrow the distance between the lens unit and the observation object to the distance according to the focal length of the refractive index distribution type lens. Hence, JP2017-020822A has room for improvements with respect to a configuration in which the excitation light is radiated.

An object of the invention is to provide a fluorescence reading device capable of narrowing a distance between a lens unit and an observation object to a distance according to a focal length of a refractive index distribution type lens and focusing fluorescence emitted from the observation object on a detecting unit without blurring.

In order to solve the above problems, a fluorescence reading device of the invention comprises an observation object holding unit that holds an observation object that is excited with excitation light to emit fluorescence; a light source that emits the excitation light; a detecting unit in which detecting elements for detecting the fluorescence are two-dimensionally arranged; a lens unit which is disposed between the observation object holding unit and the detecting unit to focus the fluorescence on the detecting unit, and on which a plurality of refractive index distribution type lenses are two-dimensionally arranged; and a light guide unit that guides the excitation light emitted from the light source to radiate the guided excitation light toward a surface of the observation object that faces the lens unit.

It is preferable that the lens unit is configured such that a plurality of lens arrays in each of which the plurality of refractive index distribution type lenses are arranged in a line in a first direction are arranged in a second direction orthogonal to the first direction, the lens unit further has a lens holding part, and the lens holding part includes a pair of parallel flat plates extending in the first direction and sandwiches and holds the lens arrays.

It is preferable that the light guide unit includes an optical fiber that guides the excitation light. In this case, it is preferable that the light guide unit includes a plurality of the optical fibers, the optical fibers are buried in the lens holding part, and emission ends of the optical fibers are exposed to a surface of the lens holding part that faces the observation object holding unit.

It is preferable that the emission ends are equally disposed within the surface of the lens holding part that faces the observation object holding unit. Additionally, it is preferable that the emission ends are disposed in a staggered lattice shape within the surface of the lens holding part that faces the observation object holding unit.

Alternatively, it is preferable that the light guide unit includes a plurality of the optical fibers, and emission ends of the optical fibers are disposed at an outer periphery of the lens unit.

It is preferable that the emission ends are directed to the observation object holding unit. Alternatively, it is preferable that the emission ends are directed to a surface of the lens holding part that faces the observation object holding unit, and the excitation light reflected by a surface of the lens holding part that faces the observation object holding unit is radiated toward the observation object holding unit. Additionally, it is preferable that the surface of the lens holding part that faces the observation object holding unit is used as a scattering surface that scatters the excitation light.

It is preferable that the light source includes a light-emitting element that emits the excitation light, an excitation light transmission filter that transmits only light within a preset wavelength range including a central wavelength of the excitation light, a condensing lens that condenses the excitation light transmitted through the excitation light transmission filter toward an incident end of the optical fiber, and a light shielding case that accommodates the light-emitting element, the excitation light transmission filter, the condensing lens, and the incident end of the optical fiber.

It is preferable that the light guide unit includes a first light guide path that is a cavity which is formed within the lens holding part and allows the excitation light to pass therethrough and that extends in the first direction within the lens holding part, a plurality of second light guide paths that each communicate with the first light guide path are disposed at intervals with respect to the first direction, and each second light guide path have one end opened toward the observation object holding unit, and a plurality of reflecting members that are disposed at intersection points between the first light guide path and the plurality of second light guide paths, respectively, and reflect the excitation light passing the first light guide path toward the second light guide paths.

It is preferable that the reflecting members include beam splitters that transmit a portion of the excitation light and reflect the remainder of the excitation light toward the second light guide paths. In this case, it is preferable that reflectivities of the beam splitters are adjusted such that light quantities of the excitation light that passes through the plurality of second light guide paths become the same, and the plurality of second light guide paths are equally disposed.

It is preferable that the light guide unit is a light guide plate having a parallel plate shape that is disposed between the observation object holding unit and the lens unit, the light guide plate has a transmission plate that transmits the excitation light and the fluorescence, a first reflective film that is formed on a surface of the transmission plate that faces the observation object holding unit and reflects the excitation light, a second reflective film that is formed on a surface of the transmission plate that faces the lens unit and reflects the excitation light, and a plurality of first openings that are portions in which the first reflective film is missing, in the surface of the transmission plate that faces the observation object holding unit, the excitation light incident from a side surface of the transmission plate is propagated through an inside of the transmission plate while being reflected by the first reflective film and the second reflective film, and a portion of the excitation light propagated through the inside of the transmission plate is emitted toward the observation object holding unit through the first openings.

It is preferable that the light guide plate further has a plurality of the second openings that are portions in which the second reflective film is missing, in the surface of the transmission plate that faces the lens unit. It is preferable that the first reflective film and the second reflective film are aluminum films, gold films, silver films, or dielectric multilayer films.

It is preferable that the second reflective film is a dielectric multilayer film that reflects the excitation light and transmits the fluorescence.

It is preferable that an exclusive area of the first openings at a central part is larger than that at an end part, in the surface of the transmission plate that faces the observation object.

The invention includes the light guide unit that guides the excitation light emitted from the light source and radiates the guided excitation light toward the surface of the observation object that faces the lens unit. The light guide unit has smaller size and shape constraints than the light source. For this reason, by using the light guide unit, various configurations in which the distance between the lens unit and the observation object is made narrow than that in the related art in which the light source is disposed between the observation object holding unit and the lens unit. For example, in a case where the focal length of the refractive index distribution type lens is about 20 mm, the distance between the lens unit and the observation object can be reliably narrowed to about 20 mm that is the focal length of the refractive index distribution type lens. Hence, it is possible that the fluorescence reading device capable of narrowing the distance between the lens unit and the observation object to the distance according to the focal length of the refractive index distribution type lens and focusing the fluorescence emitted from the observation object on the detecting unit without blurring.

BRIEF DESCRIPTION OF THE DRAWINGS

FIG. 3 is an enlarged plan view of the lens unit.
FIG. 4 is a view illustrating an aspect in which the entire lower surface of the observation object holding unit is equally irradiated with excitation light in a state where a distance between a lower surface of an observation object holding unit and an upper surface of a lens holding part coincides with the focal length of a refractive index distribution type lens.

FIG. 5 is a view illustrating a lens unit, a moving mechanism, and a movement controller. FIG. 6A illustrates a case where the lens unit is at a first position, and FIG. 6B illustrates a case where the lens unit is located at a second position.

FIG. 18 is a table illustrating an example of reflectivities of reflecting members.

FIG. 25 is a plan view illustrating a light guide plate in which circular first openings are formed.

DESCRIPTION OF THE PREFERRED EMBODIMENTS

First Embodiment

Figure 1:
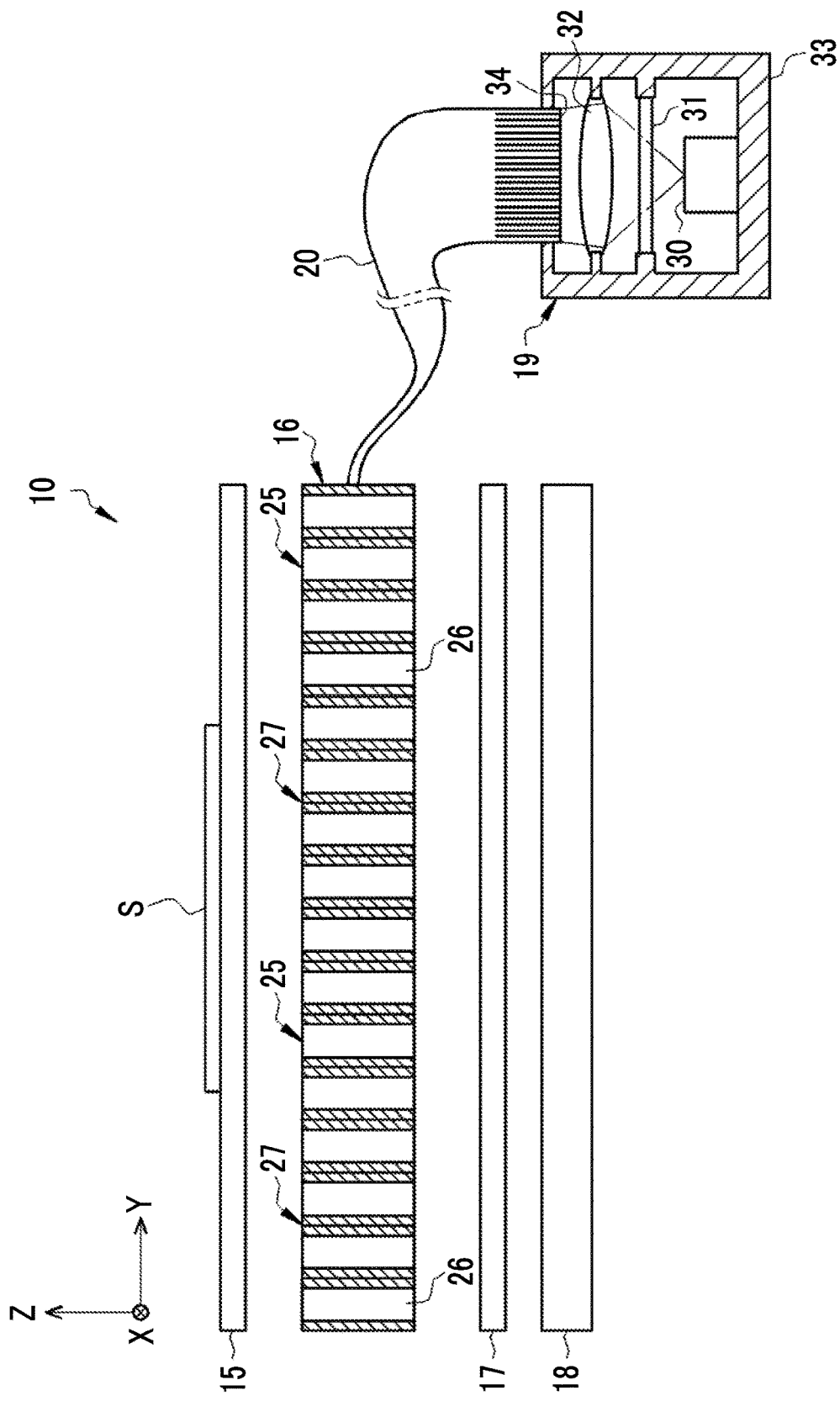
FIG. 1 is a view illustrating a fluorescence reading device.

As illustrated in FIG. 1, a fluorescence reading device 10 is a device that detects fluorescence that is excited with excitation light and emitted from an observation object S, and generates and displays a fluorescence image according to this fluorescence. The fluorescence reading device 10 includes an observation object holding unit 15, a lens unit 16, an excitation light cutoff filter 17, a detecting unit 18, a light source 19, and an optical fiber bundle 20 equivalent to a light guide unit.

The observation object holding unit 15, the lens unit 16, the excitation light cutoff filter 17, and the detecting unit 18 are disposed in this order in a Z-axis direction. Additionally, the respective parts 15 to 18 all have outer shapes that are parallel plate shapes, and are disposed such that upper surfaces and lower surfaces thereof become parallel to an XY plane including an X-axis and a Y-axis orthogonal to this. In addition, an X-axis direction corresponds to a first direction, and a Y-axis direction corresponds to a second direction. A Z-axis is an axis perpendicular to both the X-axis and the Y-axis.

The observation object holding unit 15 holds the observation object S. More specifically, the observation object holding unit 15 has the observation object S placed on the upper surface thereof. The observation object holding unit 15 is formed of materials, such as glass or resin, which allow the excitation light and the fluorescence to be transmitted therethrough.

The lens unit 16 is disposed between the observation object holding unit 15 and the excitation light cutoff filter 17 and further between the observation object holding unit 15 and the detecting unit 18. The lens unit 16 focuses the fluorescence on the detecting unit 18.

The lens unit 16 has a lens array 25. In the lens array 25, a plurality of refractive index distribution type lenses 26 are arranged in one row in a line in the X-axis direction that is the first direction (refer to FIG. 2 and the like). The lens unit 16 has a configuration in which a plurality of the lens arrays 25 are arranged in the Y-axis direction that is the second direction. That is, the lens unit 16 has a configuration in which the plurality of refractive index distribution type lenses 26 are two-dimensionally arranged in the XY plane. In addition, in the lens array 25, the refractive index distribution type lenses 26 may be arranged in two or more rows.

Each refractive index distribution type lens 26 has a columnar outer shape of which the diameter is, for example, about 0.1 mm to 5 mm. The refractive index distribution type lens 26 is, specifically, a SELFOC (registered trademark) lens.

Moreover, the lens unit 16 has a lens holding part 27. The lens holding part 27 is constituted of a pair of parallel flat plates extending in the X-axis direction, and sandwiches and holds the lens arrays 25 (refer to FIG. 2). The lens arrays 25 adjacent to each other in the Y-axis direction are separated from each other by two lens holding parts 27. The lens holding parts 27 are formed of, for example, black resin, and has a fluorescence shielding property.

The excitation light cutoff filter 17 has a spectral characteristic in which that the excitation light is not literally transmitted, and hinders incidence of the excitation light to the detecting unit 18. Meanwhile, the excitation light cutoff filter 17 has a spectral characteristic that the fluorescence is transmitted from the observation object S. For the fluorescence image generated on the basis of the fluorescence, the excitation light becomes noise. Hence, an S/N ratio of the fluorescence image can be improved by providing the excitation light cutoff filter 17.

In the detecting unit 18, a plurality of detecting elements are two-dimensionally arranged. Each detecting element detects the fluorescence transmitted through the observation object holding unit 15, the lens unit 16, and the excitation light cutoff filter 17, and outputs a detection signal. The detecting unit 18 has a detection plane for detecting the fluorescence on the upper surface thereof. The detecting unit 18 is, for example, a flat panel detector (FPD), a charge-coupled device (CCD) type detector, a complementary metal-oxide semiconductor (CMOS) type detector, or the like. The size of the detecting elements that constitute the detecting unit 18 is, for example, 50 square μm to 100 square μm. Additionally, although the size of the detection plane of the detecting unit 18 can be appropriately changed in accordance with to the size of the observation object S, the size is, for example, 10 cm square.

The light source 19 has a light-emitting element 30, an excitation light transmission filter 31, a condensing lens 32, and a case 33. The light-emitting element 30 is a light-emitting diode (LED), and emits the excitation light toward the excitation light transmission filter 31. The excitation light transmission filter 31 has a spectral characteristic that only light of a preset wavelength range including a central wavelength of the excitation light is transmitted therethrough. That is, in the excitation light emitted from the light-emitting element 30, an excessive component that may become the noise of the fluorescence image is removed by the excitation light transmission filter 31. The condensing lens 32 condenses the excitation light transmitted through the excitation light transmission filter 31 toward an incident end 34 of the optical fiber bundle 20.

The case 33 has a light shielding property. The case 33 accommodates the light-emitting element 30, the excitation light transmission filter 31, the condensing lens 32, and the incident end 34 of the optical fiber bundle 20.

The optical fiber bundle 20 guides the excitation light that is incident from the incident end 34. At the incident end 34 of the optical fiber bundle 20, a plurality of well-known optical fibers each having a core and a clad are bundled. The bundled optical fiber bundle 20 is wired toward the lens unit 16. Then, the bundled optical fiber bundle 20 is subdivided into a predetermined number of optical fiber sub-bundles 20A (refer to FIG. 2) in front of the lens unit 16. In addition, the predetermined number is within a range of, for example, one to several tens. In a case where the predetermined number is one, an optical fiber sub-bundle 20A becomes an optical fiber itself. However, in order to distinguish the optical fiber sub-bundle from the optical fiber bundle 20, optical fiber sub-bundles also including one optical fiber are referred to as the optical fiber sub-bundles 20A for convenience.

Figure 2:
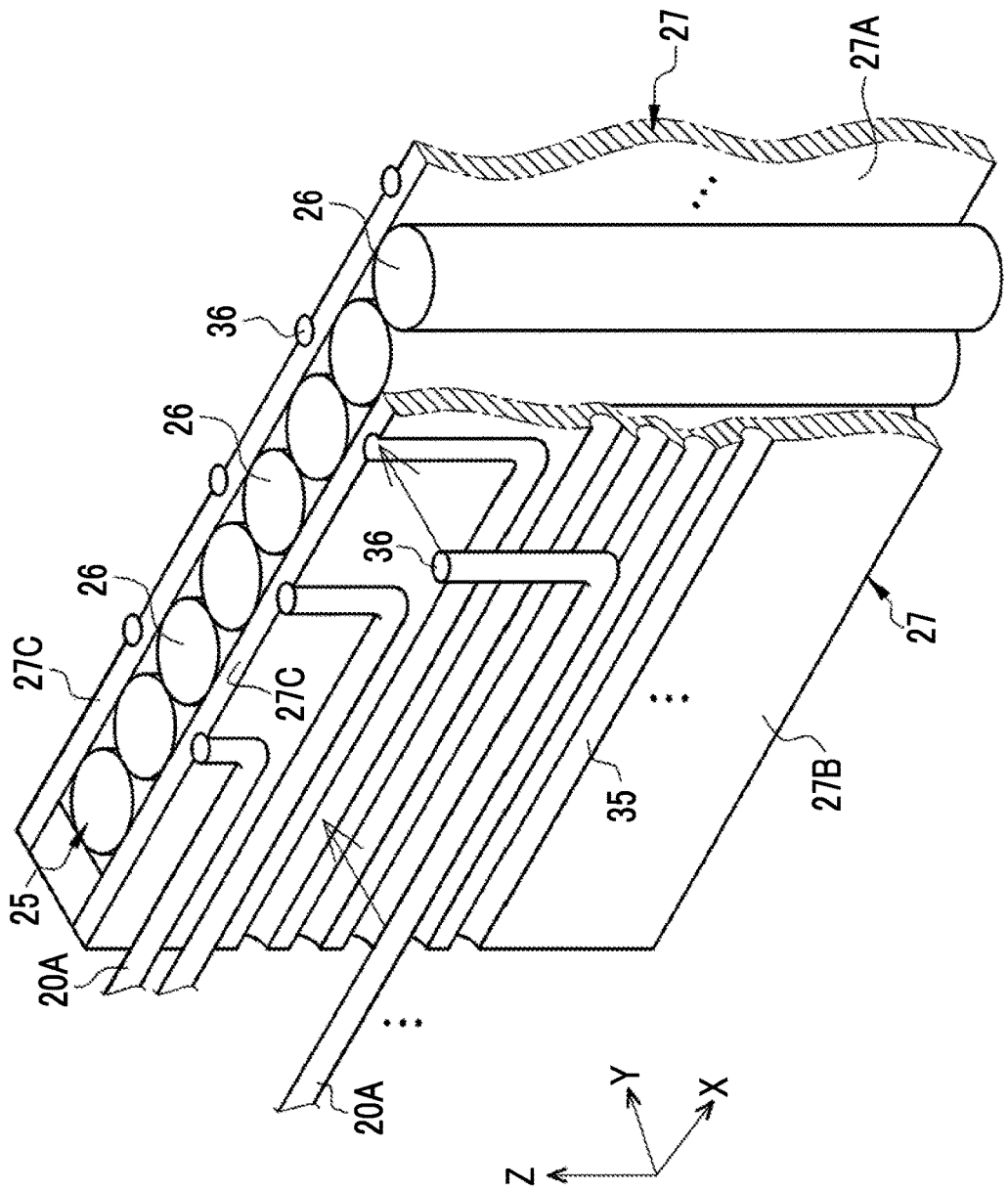
FIG. 2 is an enlarged perspective view of a lens unit.

In FIGS. 2 and 3, the optical fiber sub-bundles 20A are buried in the lens holding parts 27 of the lens unit 16. Specifically, the optical fiber sub-bundles 20A are fitted into attachment grooves 35 formed in the lens holding parts 27 as illustrates by arrows in FIG. 2.

The attachment grooves 35 are formed on surfaces 27B opposite to surfaces 27A of the lens holding parts 27 that hold each lens array 25 therebetween. Each attachment groove 35 is formed at the same position in the two lens holding parts 27 separating the adjacent lens arrays 25 from each other. That is, the attachment groove 35 has a so-called half-split shape in which a cylindrical cavity for accommodating each optical fiber sub-bundle 20A is formed by the two lens holding parts 27 being joined to each other in the surfaces 27B.

The attachment groove 35 has a portion that extends parallel to the X-axis direction from an end part of each lens holding part 27, and a portion that rises from a portion perpendicularly in the Z-axis direction. An end part including an emission end 36 of the optical fiber sub-bundle 20A is located in the portion of the attachment groove 35 that rises perpendicularly in the Z-axis direction. The emission end 36 is exposed to a surface (hereinafter, an upper surface) 27C of the lens holding part 27 that faces the observation object holding unit 15. In addition, the attachment groove 35 may be raised at an obtuse angle from the portion extending parallel to the X-axis direction such that a bending load is not applied to the optical fiber sub-bundle 20A.

The excitation light from the light source 19 is radiated toward the observation object S of the observation object holding unit 15 from the emission end 36. The surface of the observation object S in contact with the observation object holding unit 15 is irradiated with the excitation light. Then, the fluorescence is emitted from the surface of the observation object S that is irradiated with this excitation light and is in contact with the observation object holding unit 15.

The attachment grooves 35 are formed in all the lens holding parts 27 other than the lens holding parts 27 disposed at both ends with respect to the Y-axis direction. Additionally, the portions of the attachment grooves 35 that rise perpendicularly in the Z-axis direction are formed at positions parallel to the Y-axis direction at equal intervals with respect to the X-axis direction. For this reason, emission ends 36 are disposed all the lens holding parts 27 other than the lens holding parts 27 disposed at both ends with respect to the Y-axis direction, and are disposed at equal intervals at on a straight line parallel to the X-axis direction, and is disposed at equal intervals at a straight line parallel to the Y-axis direction. Hence, it can be said that the emission ends 36 are equally disposed within the XY plane (the upper surfaces 27C of the lens holding parts 27). In addition, the numbers of optical fiber sub-bundles 20A to be buried in the two lens holding parts 27 separating the adjacent lens arrays 25 from each other are several to several tens.

As illustrated in FIG. 4, a distance H between the lower surface of the observation object holding unit 15 and the upper surface 27C of each lens holding part 27 coincides with the focal length (for example, 20 mm) of the refractive index distribution type lens 26. In this state, the excitation light illustrated by one-dot chain lines is emitted at a predetermined emission angle from each emission end 36, and is equally radiated to the entire lower surface of the observation object holding unit 15. In other words, in a case where the distance H between the lower surface of the observation object holding unit 15 and the upper surface 27C of the lens holding part 27 is made to coincide with the focal length of each the refractive index distribution type lens 26, the number and the arrangement of emission ends 36, and the emission angle are set such that the excitation light is equally radiated to the entire lower surface of the observation object holding unit 15.

In FIG. 5, the moving mechanism 40 is connected to the lens unit 16. The moving mechanism 40 moves the lens unit 16 in Y-axis direction. The moving mechanism 40 is a well-known mechanism, such as a cam, which converts a rotational motion of a motor into a translational motion. A movement controller 41 that controls the operation of the moving mechanism 40 is connected to the moving mechanism 40.

Although the fluorescence from the observation object S is focused on the detecting unit 18 by the refractive index distribution type lenses 26 of the lens unit 16, a portion thereof is shielded by the lens holding part 27 having a fluorescence shielding property and does not reach the detecting unit 18. Hence, the fluorescence image has no image information of a portion corresponding to the lens holding part 27 as it is. Thus, the movement controller 41 moves the lens unit 16 to a plurality of positions in the Y-axis direction through the moving mechanism 40.

Figure 6A:
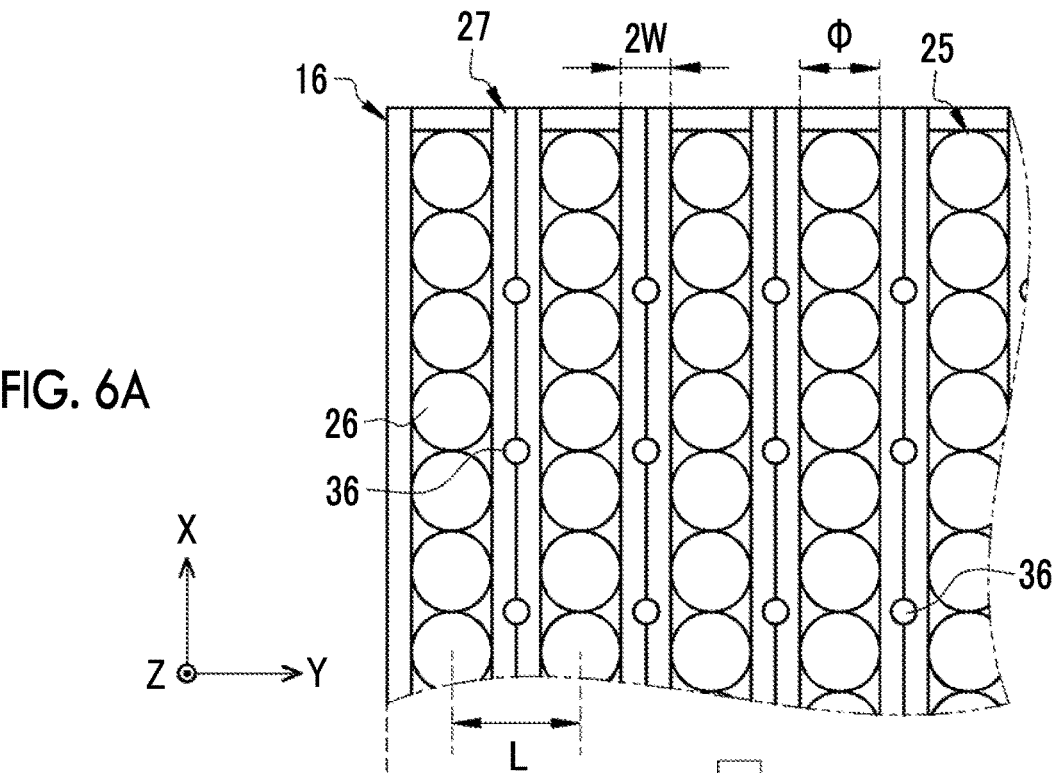
FIGS. 6A and 6B are views for illustrating the movement of the lens unit.
Figure 6B:
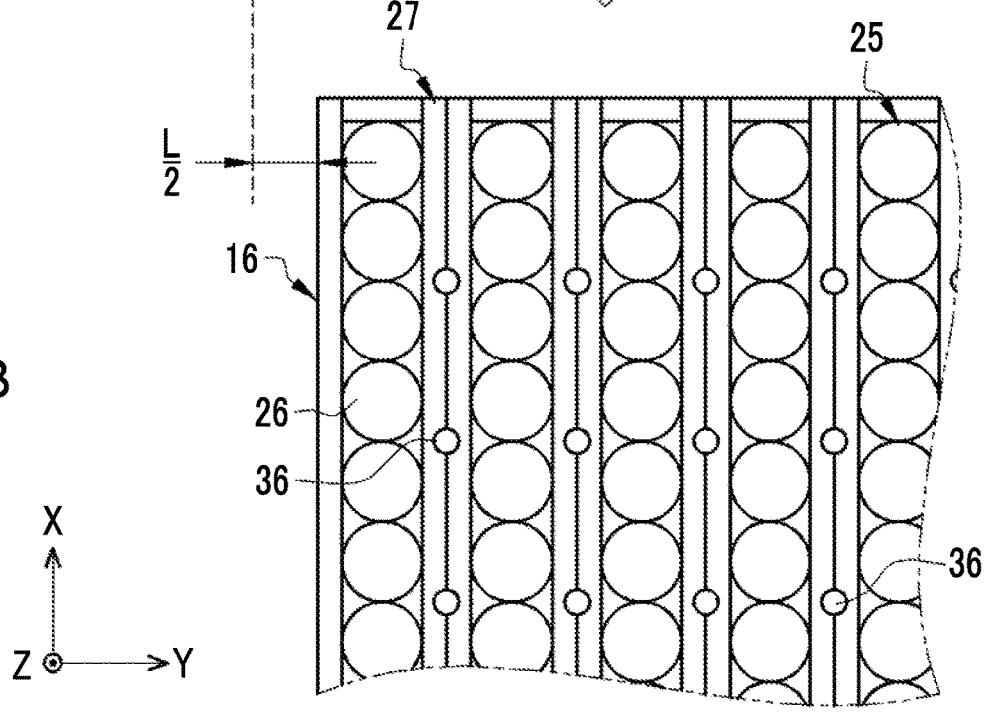

FIG. 6 has illustrated a case ($\Phi \geq 2W$) where a diameter $\Phi$ of each refractive index distribution type lens 26 is equal to or more than a width 2W equivalent to two times the width W of the lens holding part 27 in the Y-axis direction. In this case, the movement controller 41 moves the lens unit 16 from a first position illustrated in FIG. 6A to a second position illustrated in FIG. 6B through the moving mechanism 40. The second position is, specifically, a position moved by a distance of L/2 in the Y-axis direction from the first position, in a case where a center-to-center distance between the adjacent lens array 25 is L. By doing so, each lens array 25 is disposed at the second position, in a portion where each lens holding part 27 is present at the first position. Hence, a situation where a portion of the fluorescence from the observation object S is shielded by the lens holding part 27 and does not reach the detecting unit 18 is solved.

In a case where the diameter $\Phi$ of the refractive index distribution type lens 26 is smaller than 2W ($\Phi < 2W$), the movement controller 41 moves the lens unit 16 to three or more positions from the first position to the second position, from the second position to a third position, and . . . through the moving mechanism 40. For example, in a case where the diameter $\Phi$ of the refractive index distribution type lens 26 is equal to W, the movement controller 41 moves the lens unit 16 from the first position to the second position and from the second position to the third position by W through the moving mechanism 40.

The movement controller 41 moves the lens unit 16 to the last position through the moving mechanism 40 and then returns the lens unit 16 to the first position again.

Figure 7:
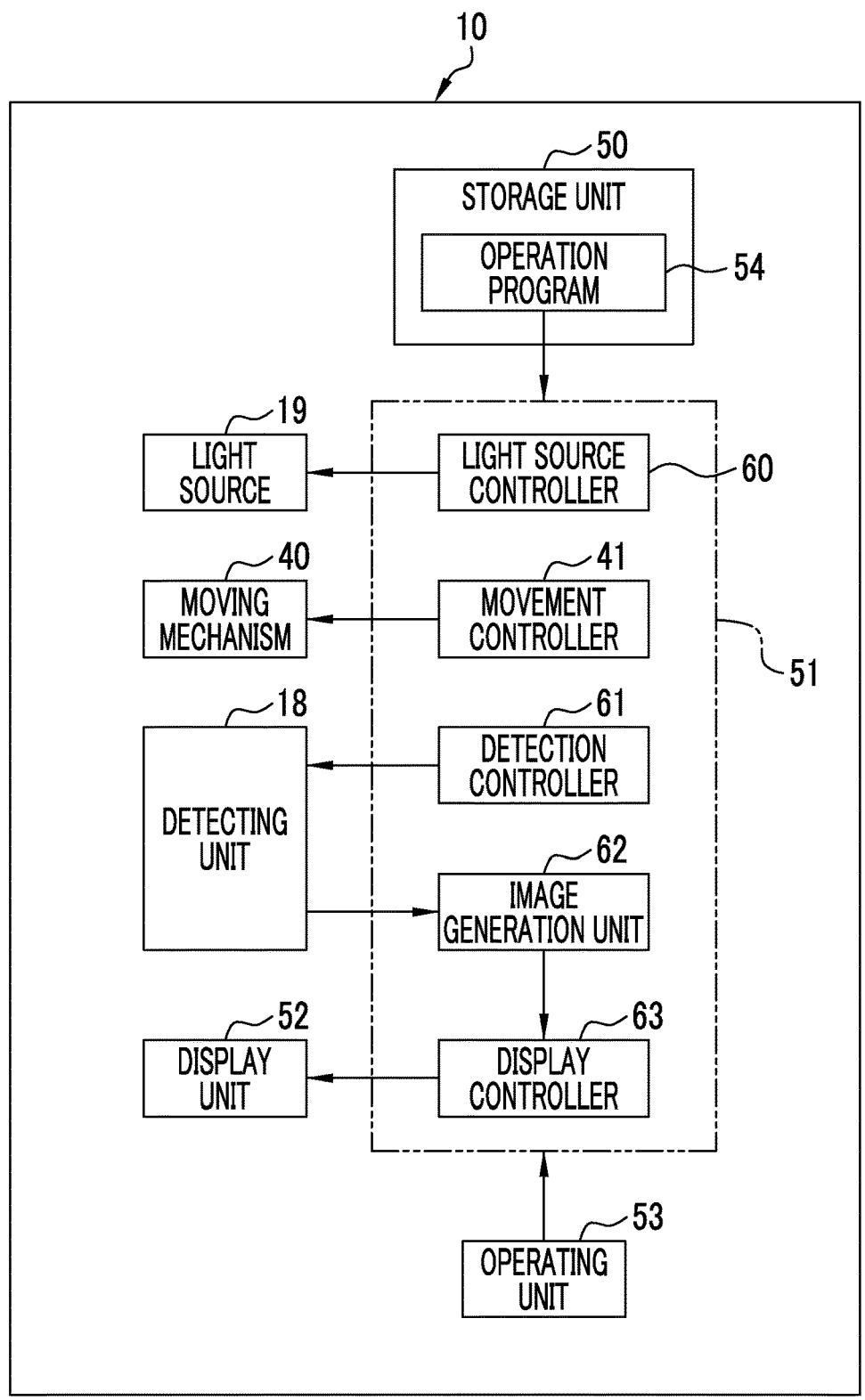
FIG. 7 is a block diagram of the fluorescence reading device.

In FIG. 7, the fluorescence reading device 10 includes a storage unit 50, a central processing unit (CPU) 51, a display unit 52, and an operating unit 53 in addition to the aforementioned detecting unit 18, light source 19, and moving mechanism 40. The storage unit 50 is, for example, a hard disk drive or the like, and stores an operation program 54. By starting the operation program 54, the CPU 51 functions as a light source controller 60, a detection controller 61, an image generation unit 62, and a display controller 63, including the aforementioned movement controller 41.

The light source controller 60 controls the operation of the light source 19, specifically, ON/OFF of the light-emitting element 30 of the light source 19. The detection controller 61 controls the operation of the detecting unit 18, specifically, the output operation of detection signals of the fluorescence by the detecting elements of the detecting unit 18. The image generation unit 62 generates the fluorescence image on the basis of the detection signals of the fluorescence from the detecting unit 18. The display controller 63 outputs the fluorescence image generated by the image generation unit 62 to the display unit 52, such as a liquid crystal display.

The detection controller 61 makes the detecting unit 18 detect the fluorescence to output the detection signals at each position of the lens unit 16 moved by the moving mechanism 40. The image generation unit 62 synthesizes the detection signals detected each time at each position to generate one fluorescence image.

Alternatively, the detection controller 61 makes the detecting unit 18 expose the fluorescence continuously from a first position to the last position, to output the detection signals, without making the detecting unit 18 output the detection signals at each position of the lens unit 16 moved by the moving mechanism 40. In this case, the image generation unit 62 generates one fluorescence image on the basis of the detection signals from the detecting unit 18 without carrying out the processing in which the detection signals detected each time at each position as described above are synthesized.

The operating unit 53 is, for example, well-known input devices, such as a keyboard and a mouse. The operating unit 53 is operated in a case where a startup instruction of the operation program 54, an imaging instruction for the fluorescence image, or the like is input.

Figure 8:
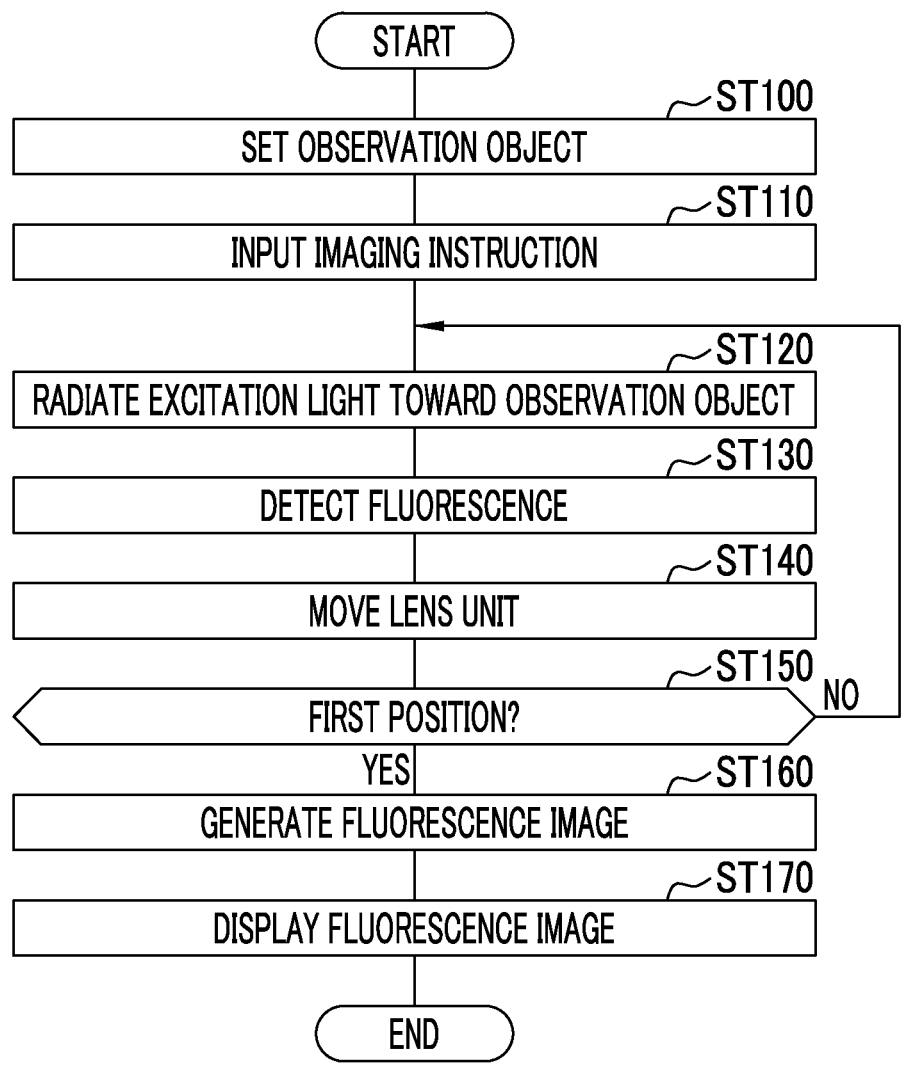
FIG. 8 is a flowchart illustrating a procedure in a case where a fluorescence image is captured by the fluorescence reading device.

Next, the operation of the fluorescence reading device 10 having the above configuration will be described with reference to a flowchart of FIG. 8. In a case where the fluorescence image is captured by the fluorescence reading device 10, the observation object S is first placed on an upper surface of the observation object holding unit 15 (Step ST100). Next, the imaging instruction for the fluorescence image is input via the operating unit 53 (Step ST110).

In a case where the imaging instruction is input via the operating unit 53, the excitation light is emitted from the light source 19 under the control of the light source controller 60. The excitation light is guided by the optical fiber bundle 20, and is radiated toward the observation object S from the emission ends 36 of the optical fiber sub-bundles 20A exposed to the upper surfaces 27C of the lens holding parts 27 (Step ST120).

The fluorescence is emitted from the observation object S by the radiation of the excitation light. The fluorescence is radiated by the detecting unit 18 via the lens unit 16 and the excitation light cutoff filter 17. This fluorescence is detected by the detecting unit 18 under the control of the detection controller 61 (Step ST130).

Subsequently, the lens unit 16 is moved through the moving mechanism 40 under the control of the movement controller 41 (Step ST140). A series of processing in these steps ST120 to ST140 is continued until the lens unit 16 is returned to the first position (YES in Step ST150).

The detection signals based on the basis of the fluorescence at a plurality of positions including the first position are output from the detecting unit 18 until the lens unit 16 is returned to the first position. In the example illustrated in FIG. 6, two detection signals based on the fluorescence at the first position and the second position are output.

After the lens unit 16 is returned to the first position, in the image generation unit 62, one fluorescence image is generated on the basis of the plurality of detection signals at individual positions, which are output from the detecting unit 18 (Step ST160). The generated fluorescence image is displayed on the display unit 52 under the control of the display controller 63 (Step ST170).

In the present example, the optical fiber bundle 20 (optical fiber sub-bundles 20A), which guides the excitation light emitted from the light source 19 and radiates the guided excitation light toward the surface of the observation object S that faces the lens unit 16, is provided. For this reason, it is not necessary to dispose the light source 19 between the observation object holding unit 15 and the lens unit 16. That is, it is not necessary to provide a space equivalent to the light source 19 between the observation object holding unit 15 and the lens unit 16. For this reason, a distance between the lens unit 16 and the observation object S can be narrowed to a distance according to the focal length of the refractive index distribution type lens 26. Hence, it is possible to focus the fluorescence emitted from the observation object S on the detecting unit 18 without blurring the fluorescence, and the image quality of the fluorescence image can be excellently maintained.

The optical fiber bundle 20 used as the light guide unit is general as an industrial product, is relatively inexpensive, and is easily obtained. Additionally, processing, such as bundling or subdividing into the optical fiber sub-bundles 20A, can be easily performed. For this reason, there is little concern about an increase in component cost and complication and a manufacturing process.

Moreover, in the present example, the optical fiber sub-bundles 20A are buried in the lens holding parts 27, and the optical fiber sub-bundles 20A are integrated with the lens holding parts 27 by exposing the emission ends 36 of the optical fiber sub-bundles 20A to the upper surfaces 27C of the lens holding parts 27. For that reason, as FIG. 4 illustrated, the distance between the lens unit 16 and the observation object S can be narrowed such that the distance H between the lower surface of the observation object holding unit 15 and the upper surface 27C of each lens holding part 27 coincides with the focal length of the refractive index distribution type lens 26.

Moreover, in the present example, since the emission ends 36 are equally disposed within the upper surface 27C of the lens holding part 27, the quantity of light of the excitation light radiated to the observation object S also becomes uniform. Hence, the excitation light can be uniformly radiated to the observation object S, and a fluorescence image with more excellent image quality can be obtained.

In addition, in a case where the excitation light emitted from each emission end 36 has a sufficient quantity of light, the number of emission ends 36 to be exposed to the upper surfaces 27C of the lens holding parts 27 can be reduced. For example, the emission ends 36 may not be disposed in all the lens holding parts 27 other than the lens holding parts 27 disposed at both ends with respect to the Y-axis direction. Specifically, as illustrated in FIG. 9, the emission ends 36 are alternately disposed in the two lens holding parts 27 separating the adjacent lens arrays 25 from each other.

Figure 10:
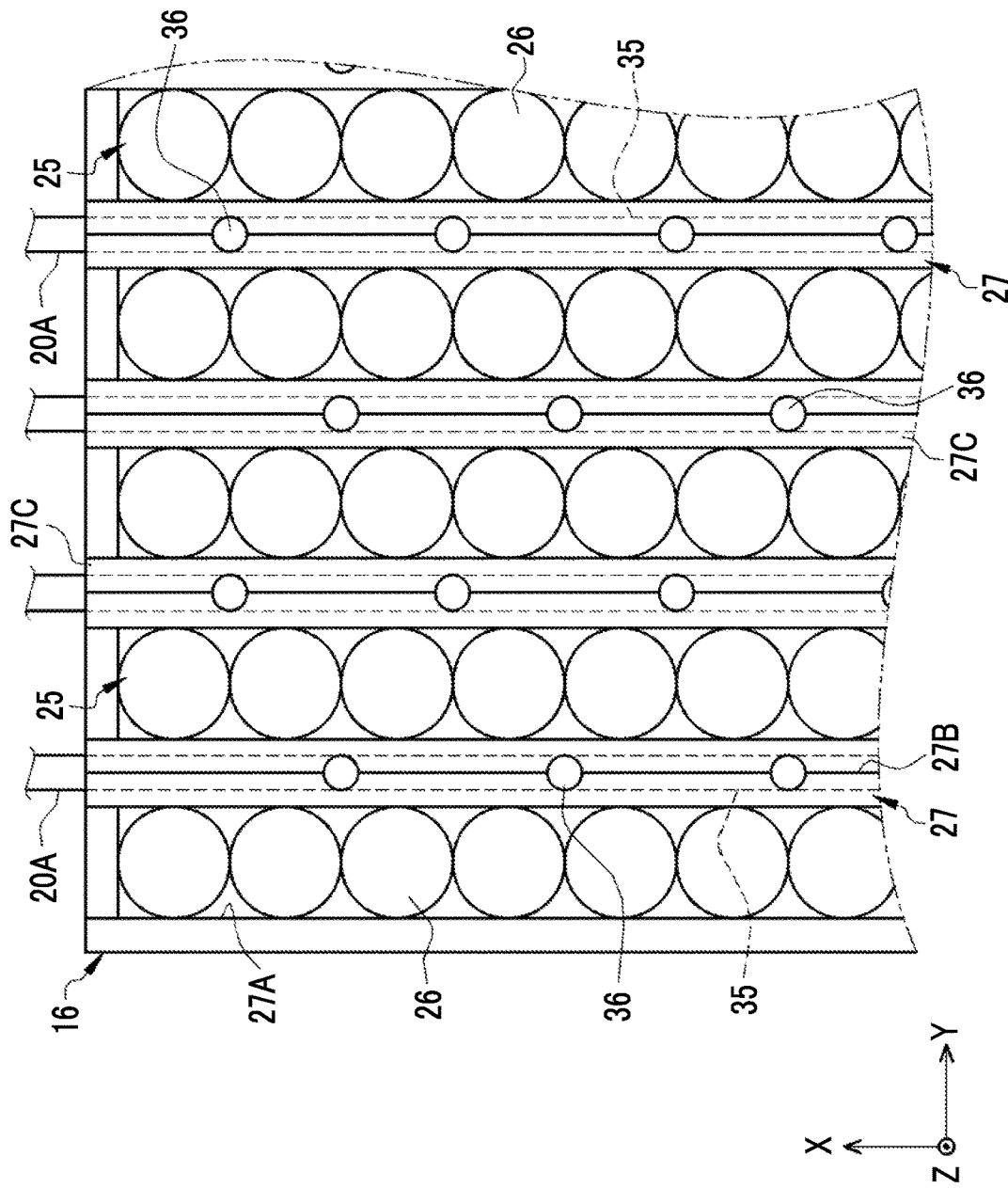
FIG. 10 is a view illustrating an example in which emission ends are disposed in a staggered lattice pattern with respect to the two lens holding parts separating the adjacent lens arrays from each other.

Additionally, the emission ends 36 may not be disposed at equal intervals on the straight line parallel to the Y-axis direction. For example, as illustrated in FIG. 10, the emission ends 36 may be disposed in a staggered lattice pattern in the two lens holding parts 27 separating the adjacent lens arrays 25 from each other. The emission ends 36 may also be disposed in a staggered lattice pattern with respect to the X-axis direction.

Figure 9:
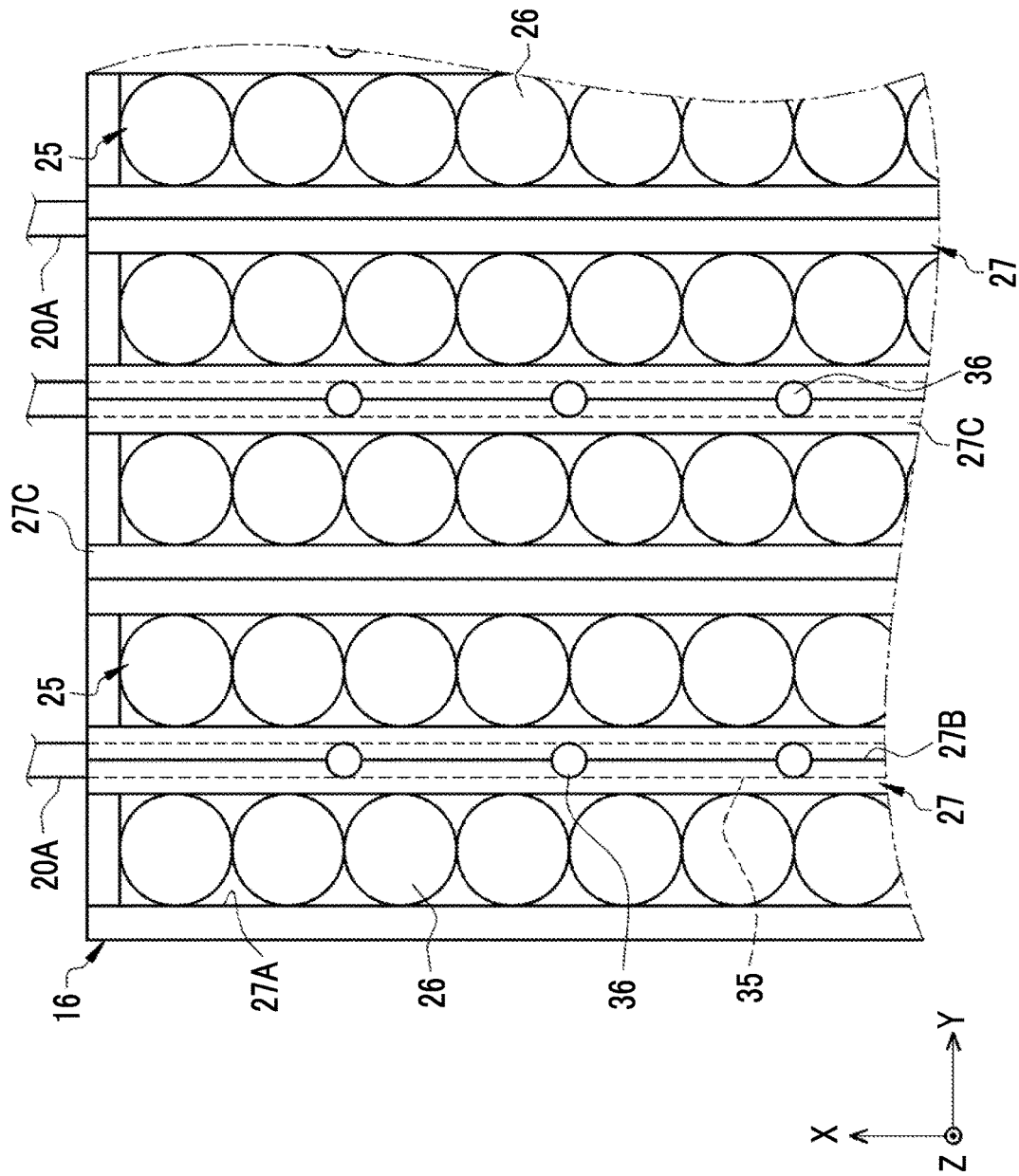
FIG. 9 is a view illustrating an example in which emission ends are alternately disposed in two lens holding parts separating adjacent lens arrays from each other.

Also in the example illustrated in these FIGS. 9 and 10, there is no change in the emission ends 36 being equally disposed within the upper surface 27C of the lens holding part 27. Hence, the effect that the excitation light can be uniformly radiated to the observation object S is obtained.

Second Embodiment

Figure 11:
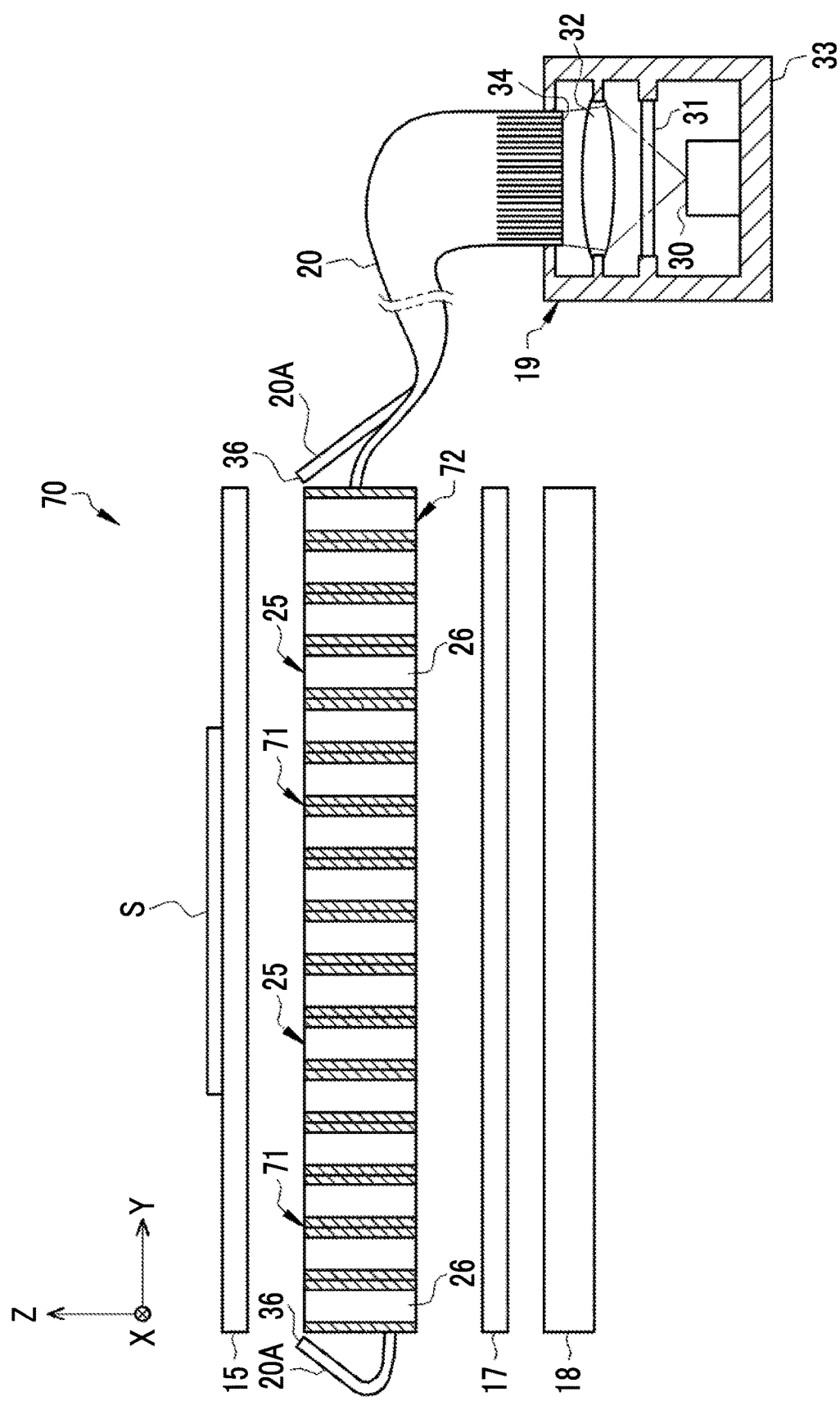
FIG. 11 is a view illustrating a fluorescence reading device of a second embodiment.
Figure 12:
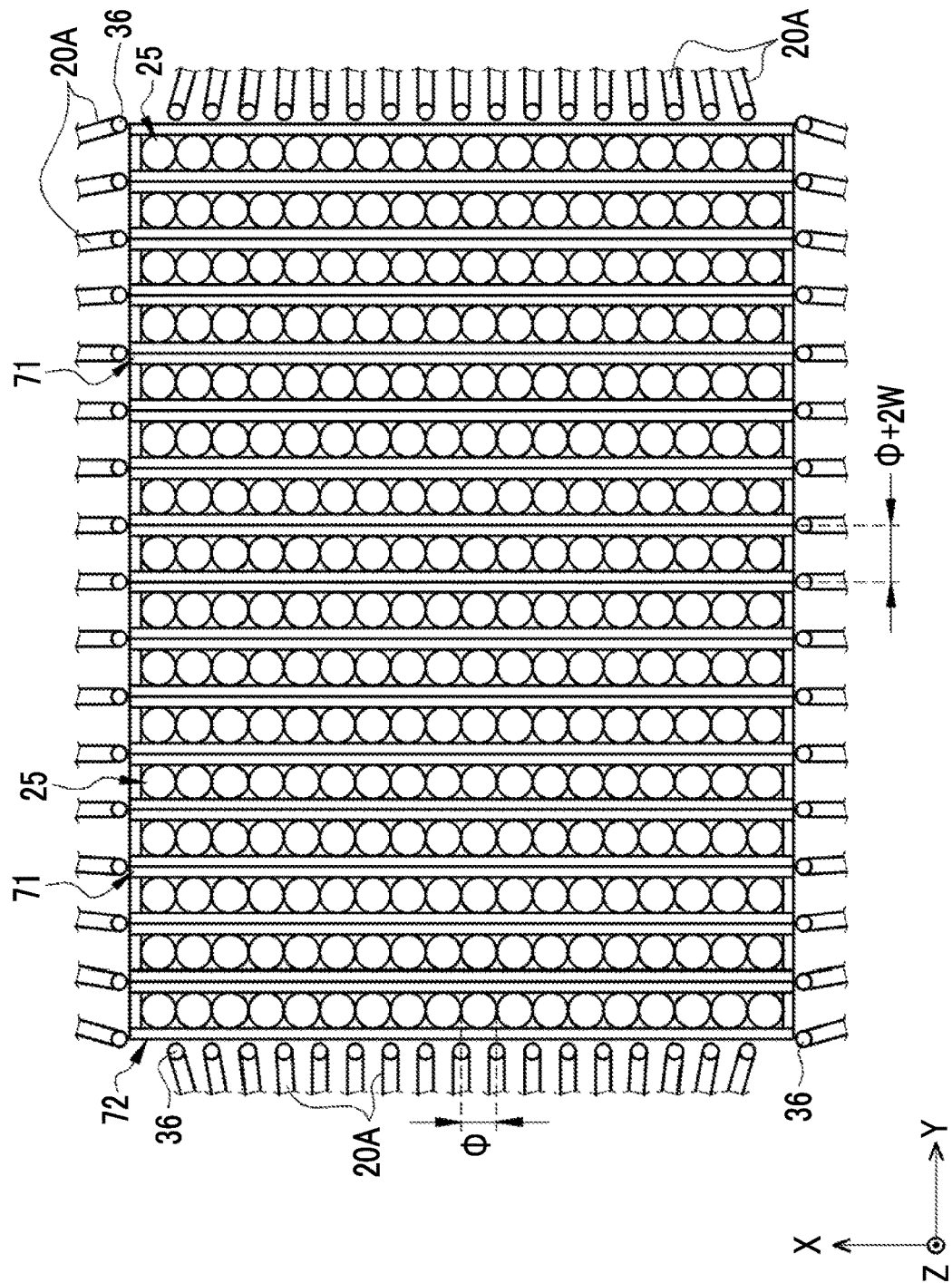
FIG. 12 is a plan view illustrating a lens unit of the second embodiment and optical fiber sub-bundles disposed around the lens unit.

A second embodiment illustrated in FIGS. 11 and 12 is an example in which the emission ends 36 of the optical fiber sub-bundles 20A are disposed at an outer periphery of the lens unit, and the emission ends 36 are directed to the observation object holding unit 15.

In FIG. 11, in a fluorescence reading device 70 of the present embodiment, a lens unit 72 in which the optical fiber sub-bundles 20A are not buried in lens holding parts 71 is used. The emission ends 36 of the optical fiber sub-bundles 20A are disposed at the outer periphery of the lens unit 72. The emission ends 36 are directed to the observation object holding unit 15. Since the other components are the same as those of the fluorescence reading device 10 of the above first embodiment, the description thereof will be omitted.

As illustrated in FIG. 12, the emission ends 36 of the optical fiber sub-bundles 20A are disposed at equal intervals so as to surround the entire outer periphery of the lens unit 72. Specifically, the emission ends 36 are lined up at the same intervals as the diameter $\Phi$ of the refractive index distribution type lens 26 with respect to the X-axis direction. Additionally, with respect to the Y-axis direction, the emission ends 36 are lined up at intervals $\Phi+2W$ obtained by summing up the diameter $\Phi$ of the refractive index distribution type lens 26 and the width $2W$ equivalent to two times the width $W$ of each lens holding part 71 in the Y-axis direction. That is, the emission ends 36 are disposed at the same pitch as the array pitches of the refractive index distribution type lenses 26 in the X-axis direction and the Y-axis direction.

In this way, the emission ends 36 of the optical fiber sub-bundles 20A are disposed at the outer periphery of the lens unit 72. Thus, it is not necessary to form the attachment grooves 35 for fitting the optical fiber sub-bundles 20A into the lens holding parts 71, as in a case where the optical fiber sub-bundles 20A of the above first embodiment are buried in the lens holding parts 27 and the emission ends 36 are exposed to the upper surfaces 27C. Hence, compared to the above first embodiment, the labor and cost of the processing of the attachment grooves 35 can be reduced.

In addition, in this case, the arrangement angle of the optical fiber sub-bundles 20A with respect to the observation object holding unit 15 is adjusted. More specifically, the portion of the observation object holding unit 15 to be handled is assigned to individual optical fiber sub-bundles 20A such that a certain optical fiber sub-bundle 20A is directed toward an end part of the observation object holding unit 15 and a certain optical fiber sub-bundle 20A is directed toward a central part of the observation object holding unit 15. Additionally, since the distance from each emission end 36 becomes longer at the central part the observation object holding unit 15 than at the end part of the observation object holding unit 15 and the excitation light is attenuated, the quantity of light is increased by making the number of optical fibers that constitute the optical fiber sub-bundles 20A that handle the central part larger than the number of optical fibers that constitute the optical fiber sub-bundles 20A that handle the end part. By taking such measures, the excitation light having the same quantity of light is radiated to the entire lower surface of the observation object holding unit 15, and the excitation light is uniformly radiated to the observation object S.

Third Embodiment

Figure 13:
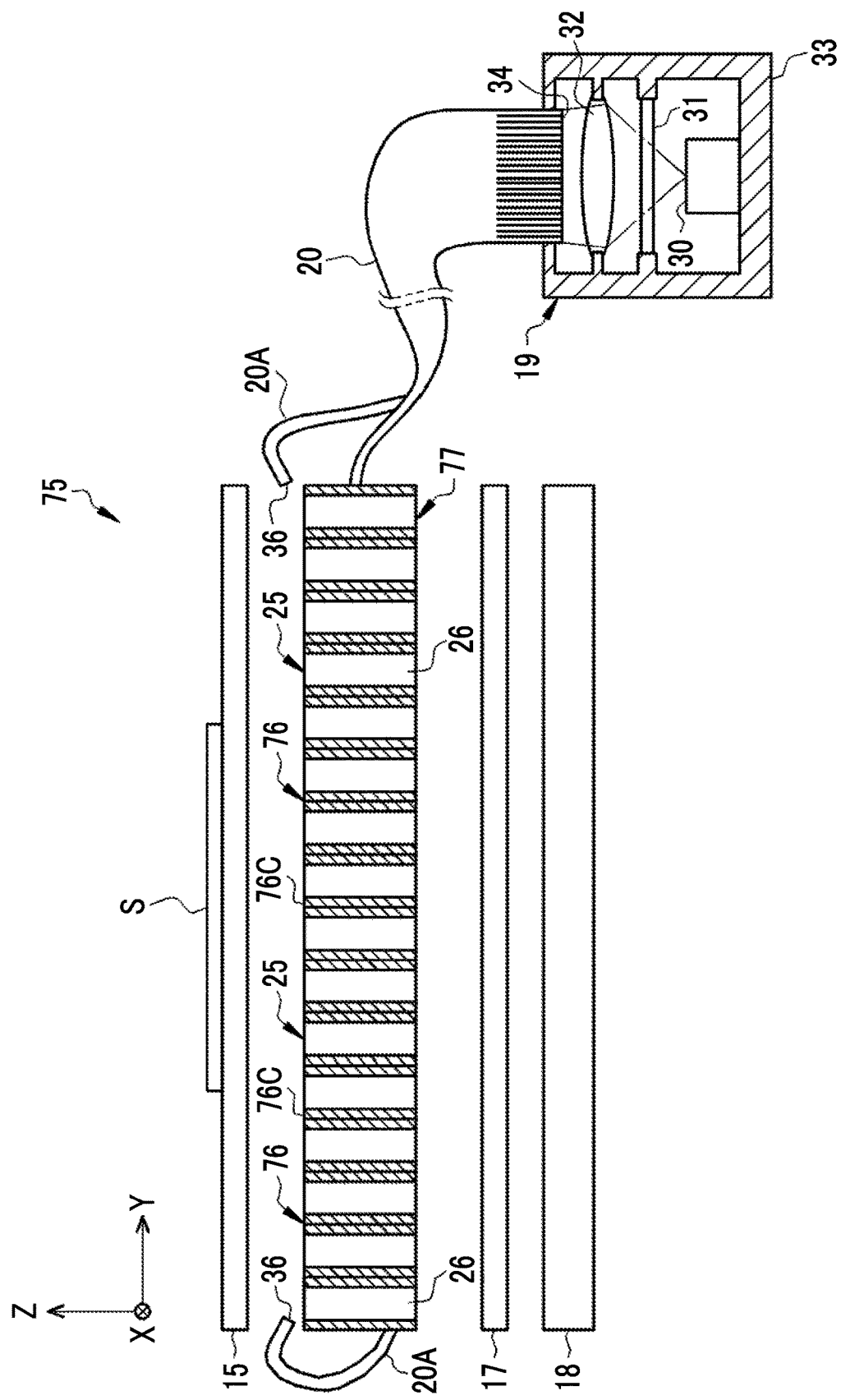
FIG. 13 is a view illustrating a fluorescence reading device of a third embodiment.
Figure 14:
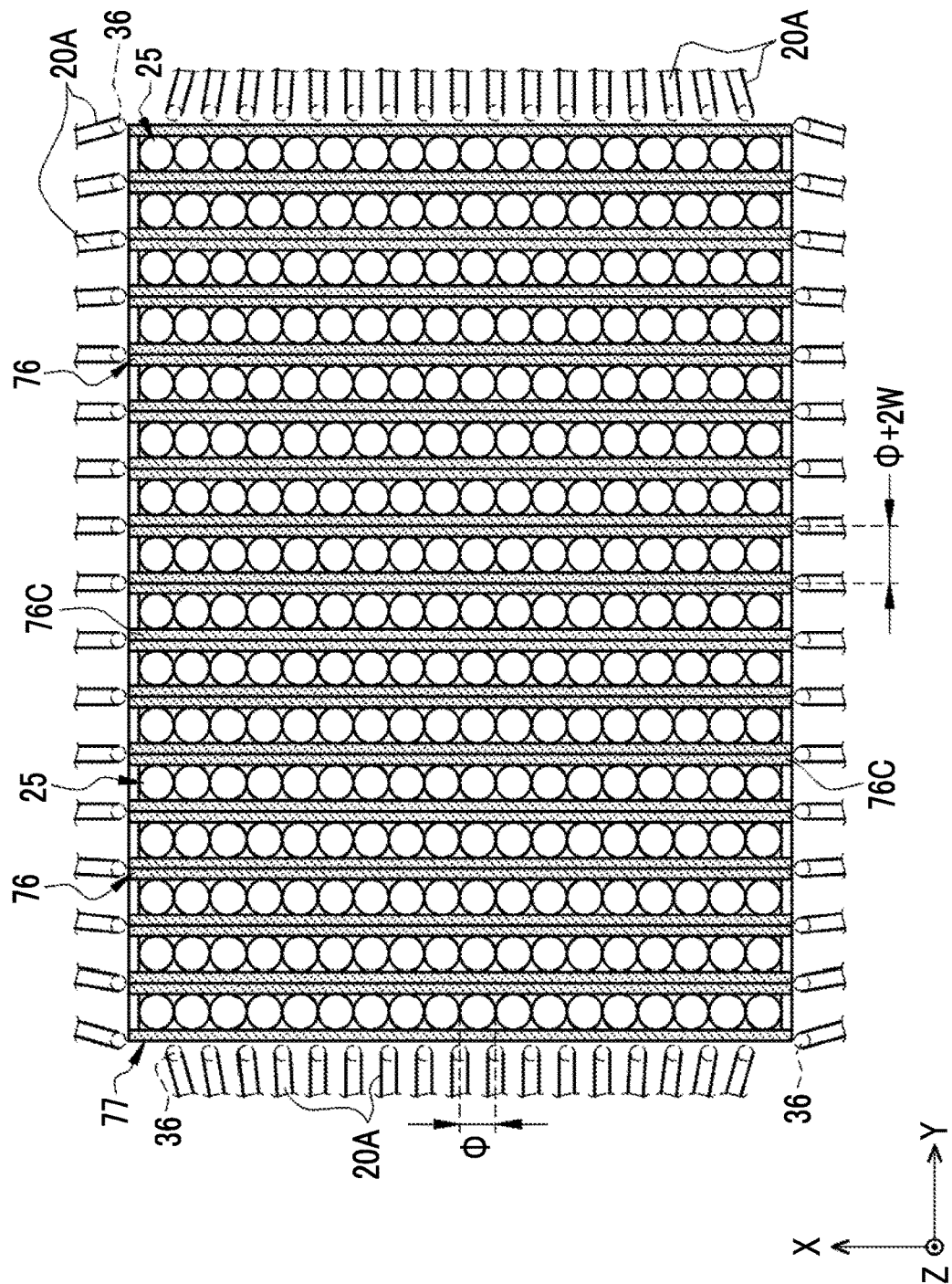
FIG. 14 is a plan view illustrating a lens unit of the third embodiment and optical fiber sub-bundles disposed around the lens unit.

The third embodiment illustrated in FIGS. 13 and 14 is an example in which the emission ends 36 of the optical fiber sub-bundles 20A are disposed at the outer periphery of the lens unit 16, and the emission ends 36 are directed not toward the observation object holding unit 15 but toward the upper surfaces of the lens holding parts that face the observation object holding unit 15.

In FIG. 13, a fluorescence reading device 75 of the present embodiment is the same as the above second embodiment in that a lens unit 77 in which the optical fiber sub-bundles 20A are not buried in lens holding parts 76, and the emission ends 36 of the optical fiber sub-bundles 20A are disposed at the outer periphery of the lens unit 77. However, the present embodiment is different from the above second embodiment in that the emission ends 36 are directed not toward the observation object holding unit 15 but toward upper surfaces 76C of the lens holding parts 76 that face the observation object holding unit 15. Since the other components are the same as those of the fluorescence reading device 10 of the above first embodiment, the description thereof will be omitted.

As illustrated in FIG. 14, similar to the above second embodiment, the emission ends 36 of the optical fiber sub-bundles 20A are disposed at equal intervals so as to surround the entire outer periphery of the lens unit 77. Additionally, similar to the above second embodiment, the intervals relating to the X-axis direction and the intervals related to the Y-axis direction are also respectively the diameter Φ of the refractive index distribution type lens 26, and intervals Φ+2W obtained by summing up the width 2W equivalent to two times the width W of each lens holding part 76 in the Y-axis direction and the diameter Φ of the refractive index distribution type lens 26.

The lens holding parts 76 are formed of a material that reflects the excitation light. Additionally, the upper surfaces 76C of the lens holding parts 76 are subjected to, for example, roughening processing, such as of sandblasting, and is made into a scattering surface, as illustrated by hatching. In this case, the excitation light emitted from the emission ends 36 is reflected and scattered by the upper surfaces 76C of the lens holding parts 76, and is radiated toward the observation object holding unit 15 from the upper surfaces 76C of the lens holding parts 76.

Even with the above configuration, similar to the above second embodiment, the effect that the labor and cost of the processing of the attachment grooves 35 can be reduced compared to the above first embodiment can be obtained.

Since the upper surfaces 76C of the lens holding parts 76 are made into the scattering surfaces, the excitation light having more uniform quantity of light can be radiated to a wider range of the observation object holding unit 15.

In addition, even in this case, similar to the above second embodiment, the arrangement angle of the optical fiber sub-bundles 20A with respect to the upper surfaces 76C of the lens holding parts 76 is adjusted such that the excitation light having the same quantity of light is radiated to the entire lower surface of the observation object holding unit 15. Additionally, the quantity of light is increased by making the number of optical fibers that constitute the optical fiber sub-bundles 20A that handle central parts of the upper surfaces 76C of the lens holding parts 76 larger than the number of optical fibers that constitute the optical fiber sub-bundles 20A that handle end parts of the upper surfaces 76C.

Additionally, it is not necessary to form all the lens holding parts 76 of the material that reflects the excitation light, and at least the upper surfaces 76C that reflect and scatter the excitation light may have a configuration in which the excitation light is reflected. For example, it is possible to coat the upper surfaces 76C with the material that reflects the excitation light.

Fourth Embodiment

The fourth embodiment illustrated in FIGS. 15 to 18 is an example in which two light guide paths formed by cavities, and a plurality of reflecting members disposed within the light guide paths constitute a light guide unit.

Figure 15:
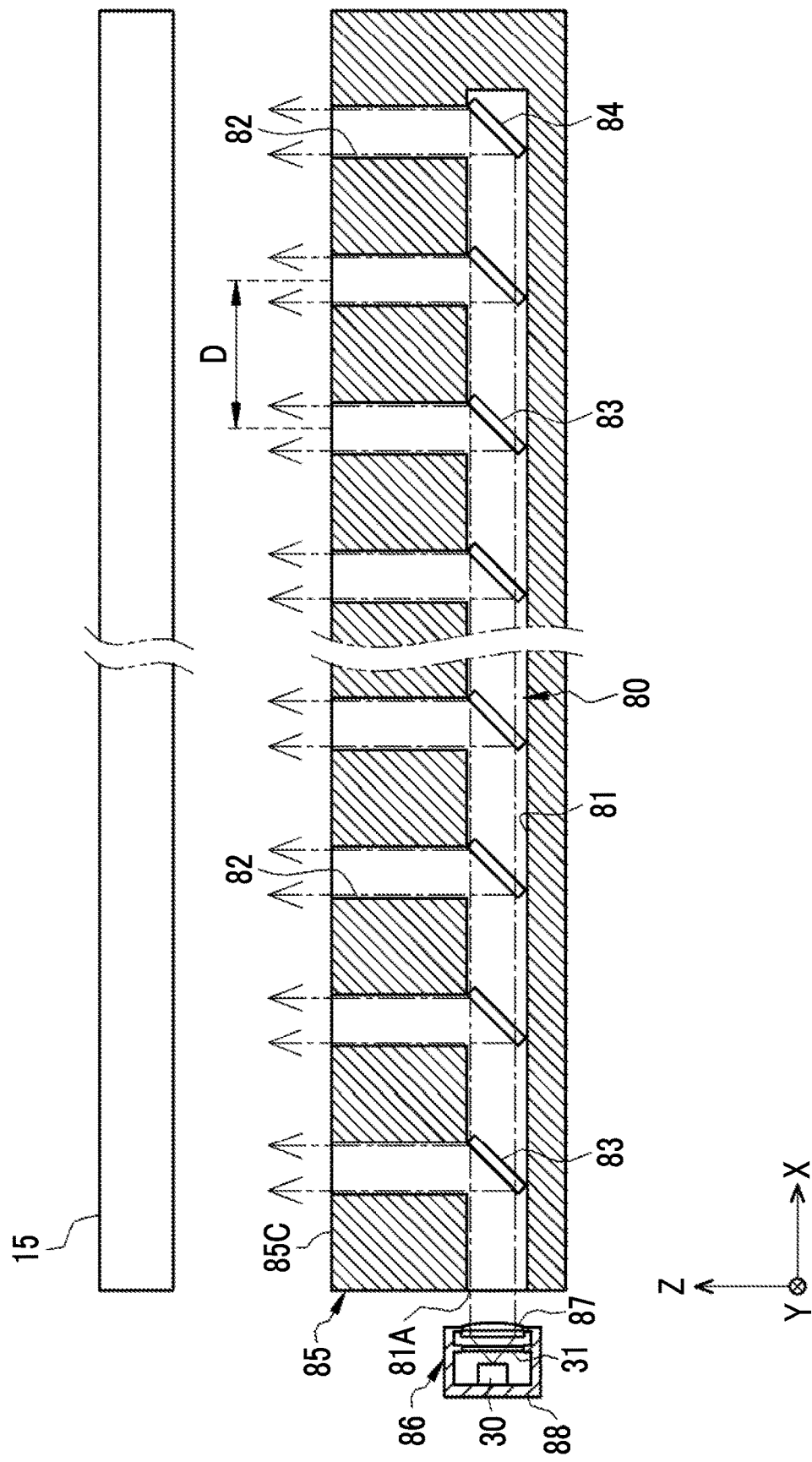
FIG. 15 is a cross-sectional view illustrating a light guide unit of a fourth embodiment.
Figure 16:
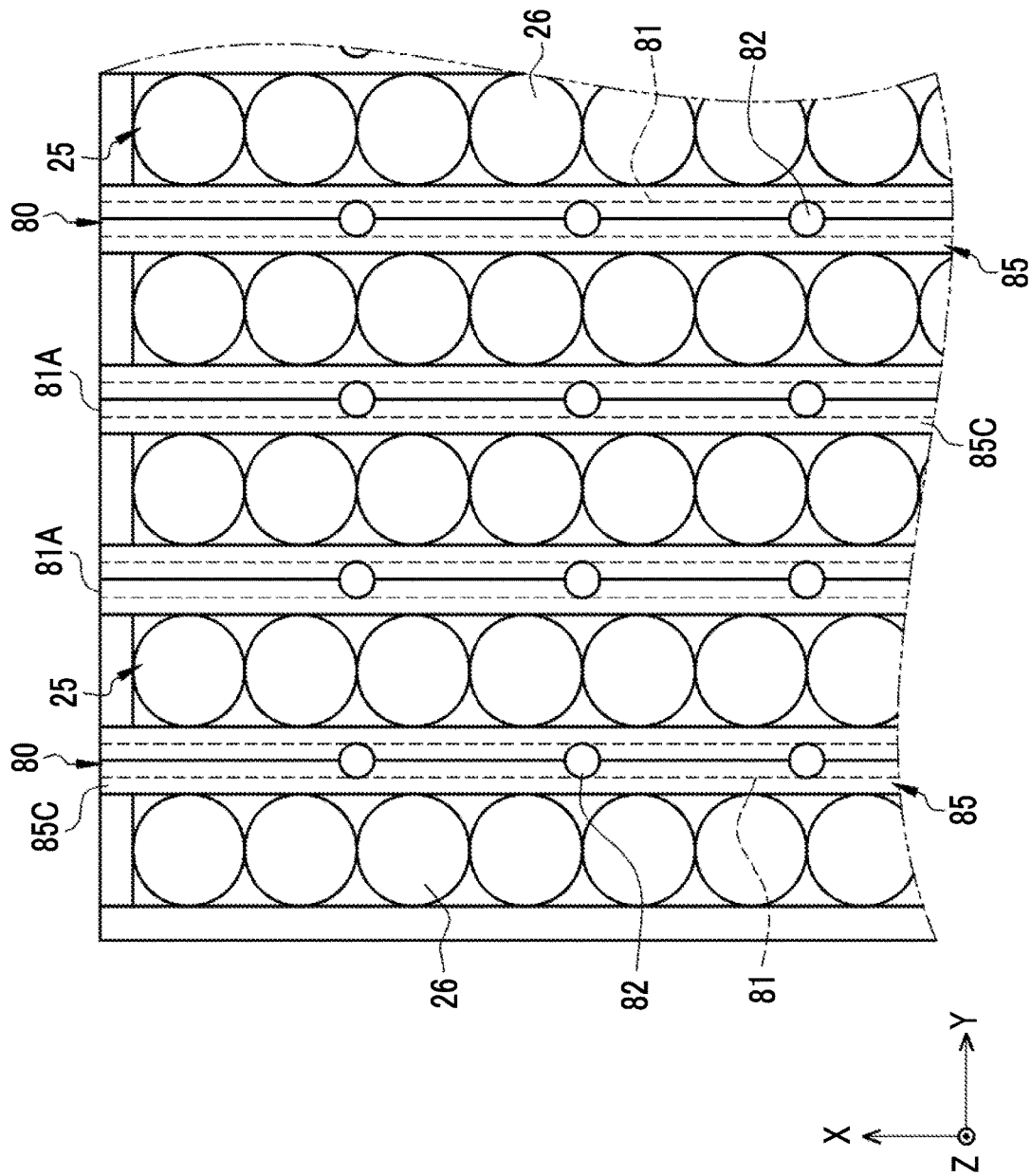
FIG. 16 is a plan view illustrating the light guide unit of the fourth embodiment.
Figure 17:
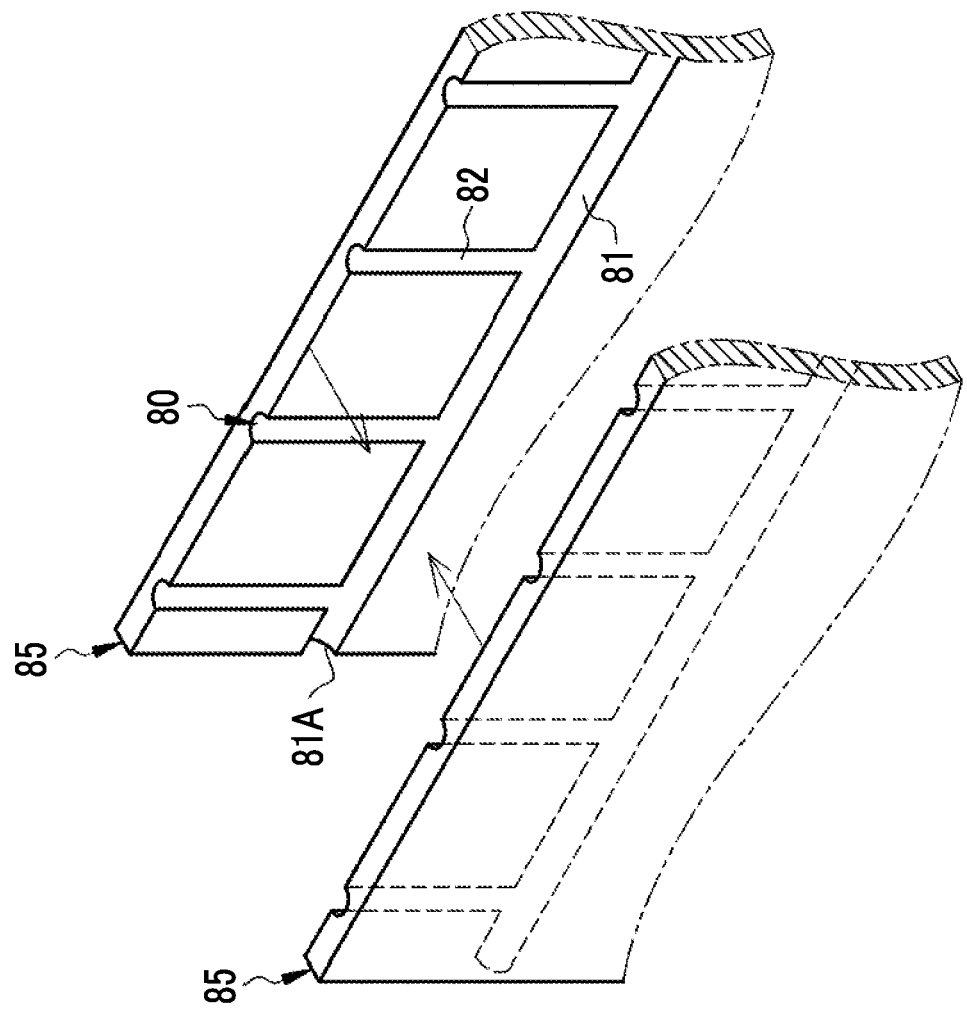
FIG. 17 is an enlarged exploded perspective view of a lens holding part of the fourth embodiment.

In FIGS. 15 to 17, a light guide unit 80 of the fourth embodiment is constituted of a first light guide path 81, a second light guide path 82, a plurality of beam splitters 83 equivalent to the reflecting members, and a total reflection mirror 84 that is also equivalent to a reflecting member (in FIGS. 16 and 17, the beam splitters 83 and the total reflection mirror 84 are not illustrated). The first light guide path 81 and the second light guide path 82 are cylindrical cavities formed within lens holding parts 85, and allow the excitation light to pass therethrough. More specifically, the first light guide path 81 and the second light guide path 82 are formed in a half-split shape in bonding surfaces of the two lens holding parts 85 separating the adjacent lens arrays 25 from each other similar to the attachment groove 35 of the above first embodiment, and the cylindrical cavities are formed by the two lens holding part 85 being joined to each other.

The first light guide path 81 extends in the X-axis direction, which is the first direction, within the lens holding parts 85. A plurality of the second light guide paths 82 are provided, and are disposed at intervals D in the X-axis direction. The plurality of second light guide paths 82 respectively communicate with the first light guide path 81 and one end of each thereof opens toward the observation object holding unit 15 (the observation object S is not illustrated). Additionally, the plurality of second light guide paths 82 are parallel to the Z-axis direction, and respectively intersect the first light guide path 81, which extends in the X-axis direction, at right angles.

The beam splitters 83 and the total reflection mirror 84 are respectively disposed at intersection points between the first light guide path 81 and the plurality of second light guide paths 82. The beam splitters 83 and the total reflection mirror 84 are disposed so as to be tilted with respect to an optical axis of the excitation light (illustrated by arrows of one-dot chain lines), which passes through the first light guide path 81, at 45°. The beam splitters 83 transmit a portion of the excitation light passing through the first light guide path 81, and reflect the remainder of the excitation light toward the second light guide paths 82. The total reflection mirror 84 is located on the most downstream side of the first light guide path 81, and reflect all the excitation light passing through the first light guide path 81 toward the second light guide paths 82.

The end of the first light guide path 81 on the most upstream side opposite to a side where the total reflection mirror 84 is disposed opens to end surfaces of the lens holding parts 85. A light source 86 that emits the excitation light is disposed at a position that faces an opening 81A of this first light guide path 81. The light source 86 has the light-emitting element 30 and the excitation light transmission filter 31, similar to the light sources 19 (refer to FIG. 1 and the like) of the above embodiments. However, the light source 86 has a collimating lens 87 instead of the condensing lens 32, and has a configuration in which the light-emitting element 30, the excitation light transmission filter 31, and the collimating lens 87 are accommodated in a case 88 having a light shielding property. The collimating lens 87 makes the excitation light, which is emitted from the light-emitting element 30 and transmitted through the excitation light transmission filter 31, into collimated light, and makes the collimated light incident on the first light guide path 81.

A portion of the excitation light incident on the first light guide path 81 is reflected by the individual beam splitters 83 and is incident the second light guide paths 82. Additionally, the excitation light is totally reflected by the total reflection mirror 84, and is incident on the second light guide paths 82. The excitation light incident on the second light guide paths 82 is emitted from openings of the second light guide paths 82, and is radiated to the lower surface of the observation object holding unit 15. In addition, although illustration is omitted, the scattering plate for making excitation light collimated by the collimating lens 87 into scattered light are disposed in the openings of the second light guide paths 82.

The intervals D of the adjacent second light guide paths 82 are all equal to each other. That is, the second light guide paths 82 are formed at equal intervals with respect to the X-axis direction. Additionally, as FIG. 16 illustrated, the second light guide paths 82 are formed in all the lens holding parts 85 other than the lens holding part 85 disposed at both ends with respect to the Y-axis direction, similar to the emission ends 36 illustrated in FIG. 3 of the above first embodiment. Moreover, the second light guide paths 82 are formed at equal intervals on a straight line parallel to the Y-axis direction. That is, the lens unit in this case has a configuration in which the emission ends 36 are substituted with the second light guide paths 82, in the lens unit 16 illustrated in FIG. 3 or 4. Hence, it can be said that the plurality of second light guide paths 82 are equally disposed within the XY plane (the upper surfaces 85C of the lens holding parts 85).

As illustrated in Table 90 of FIG. 18, the reflectivities of the beam splitters 83 are adjusted such that the light quantities of the excitation light that passes through the plurality of second light guide paths 82 become the same. Table 90 shows reflectivities of the individual beam splitters 83 in the case of the number of the reflecting members (the beam splitters 83 and the total reflection mirror 84) (the number of the second light guide paths 82)=10, and reflected light quantities and transmitted light quantities in a case where the light quantity of the excitation light that is first incident on the first light guide path 81 from the light source 86 is 100. Additionally, Table 90 shows that, as No. is smaller, a reflecting mirror is at a position closer to the light source 86 side, that is, at a position closer to the upstream side of the first light guide path 81.

The reflectivities increase toward the downstream side. The most downstream No. 10 is the total reflection mirror 84, and the reflectivity thereof is 100%. In the example of Table 90, since the number of second light guide paths 82=10, the reflectivity is adjusted such that the light quantities (reflected light quantities) of the excitation light passing through the ten second light guide paths 82 are the same "10".

In addition, the expression the "light quantities of the excitation light that passes through the plurality of second light guide paths 82 are same" includes not only completely the same but also allow some variations. In the example of Table 90, although the reflected light quantities of the beam splitter 83 of Nos. 1, 3, 6, and 7 are "10.00", the reflected light quantity of Nos. 2, 9, and 10 are "9.99", the reflected light quantity of No. 4 is "10.01", the reflected light quantities of Nos. 5 and 8 are "10.02", and somewhat vary from each other. However, since these reflected light quantities all become "10" in a case where the reflected light quantities are rounded off at two decimal points, it is assumed that the "light quantities of the excitation light that passes through the plurality of second light guide paths 82 are same". In addition, a range where the variations are allowed is, for example, a range where the reflected light quantities coincide with each other in a case where the reflected light quantities are rounded off at two decimal points. This is based on manufacturing errors of the reflecting members, such as the beam splitters 83 and the total reflection mirror 84, being about ±5%.

In this way, since the light guide unit 80 is constituted of the first light guide path 81, the second light guide paths 82, the beam splitters 83, and the total reflection mirror 84, it is not necessary to prepare the optical fiber bundle 20 unlike the above individual embodiments. For this reason, the cost for the optical fiber bundle 20 can be reduced.

Since the reflectivities of the beam splitters 83 are adjusted such that the light quantities of the excitation light that passes through the plurality of second light guide paths 82 become the same and the plurality of second light guide paths 82 are equally disposed, the excitation light can be uniformly radiated to the observation object S.

For example, similar to the example illustrated in FIG. 9, the second light guide paths 82 may not be disposed in all the lens holding parts 85 other than the lens holding parts 85 disposed at both ends with respect to the Y-axis direction. Additionally, similar to the example illustrated in FIG. 10, the second light guide paths 82 may be disposed in a staggered lattice pattern in the two lens holding parts 85 separating the adjacent lens arrays 25 from each other.

Although the light source 86 is disposed at the position that faces the opening of the first light guide path 81, in this case, it is necessary to dispose the light source 86 by the amount equivalent to the first light guide path 81. Thus, the light source 19 of each of the above embodiments may be used instead of the light source 86, and the emission ends 36 of the optical fiber sub-bundles 20A may be disposed at positions that face the opening of the first light guide path 81. In this case, the optical fiber bundle 20 (optical fiber sub-bundles 20A) is also included in the light guide unit 80.

The second light guide paths 82 need not be orthogonal to the first light guide path 81. The second light guide paths 82 may intersect the first light guide path 81 at an acute angle or an obtuse angle.

Fifth Embodiment

A fifth embodiment illustrated in FIGS. 19 to 25 is an example in which a light guide plate having a parallel plate shape constitute a light guide unit.

Figure 19:
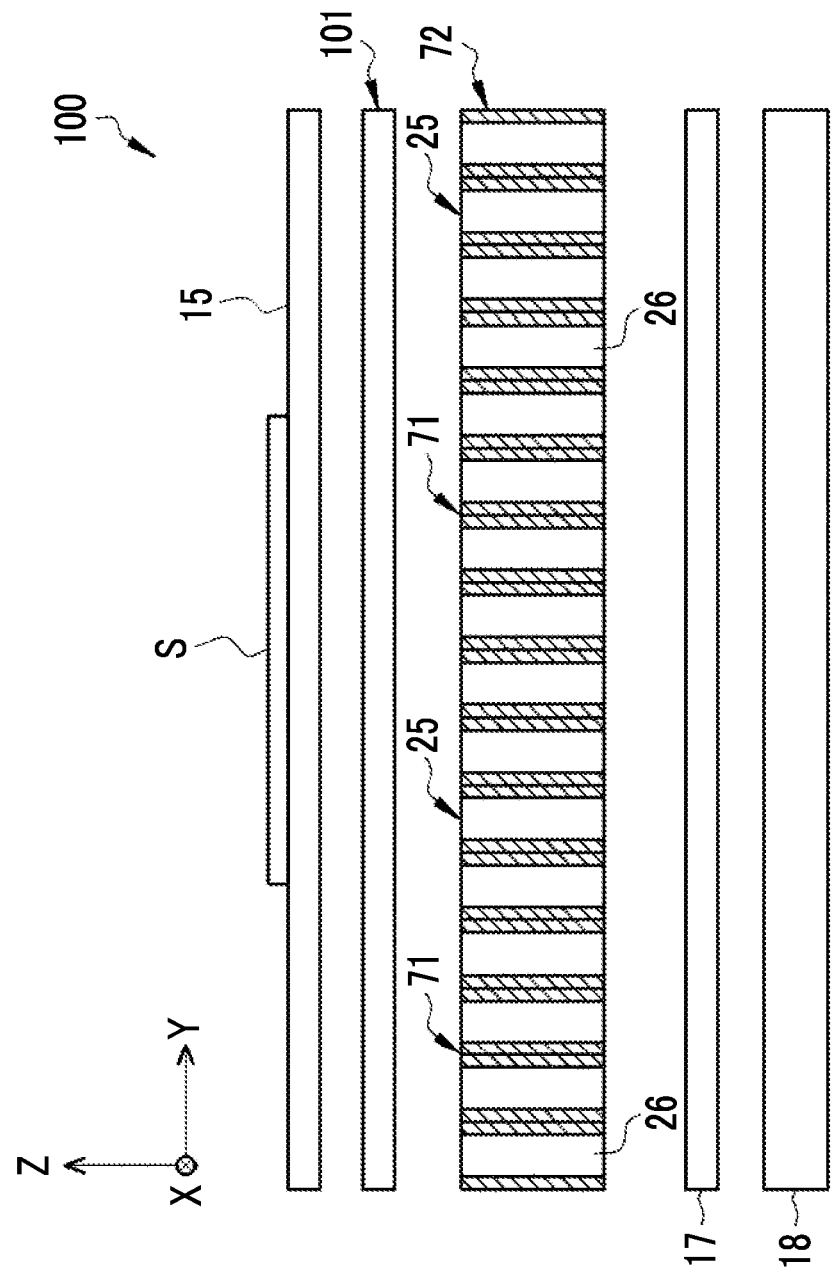
FIG. 19 is a view illustrating a fluorescence reading device of a fifth embodiment.

In FIG. 19, a fluorescence reading device 100 of the present embodiment includes a light guide plate 101 having a parallel plate shape, as the light guide unit. The lens unit 72 of the above second embodiment is used for the lens unit. The light guide plate 101 is disposed between the observation object holding unit 15 and the lens unit 72.

Figure 20:
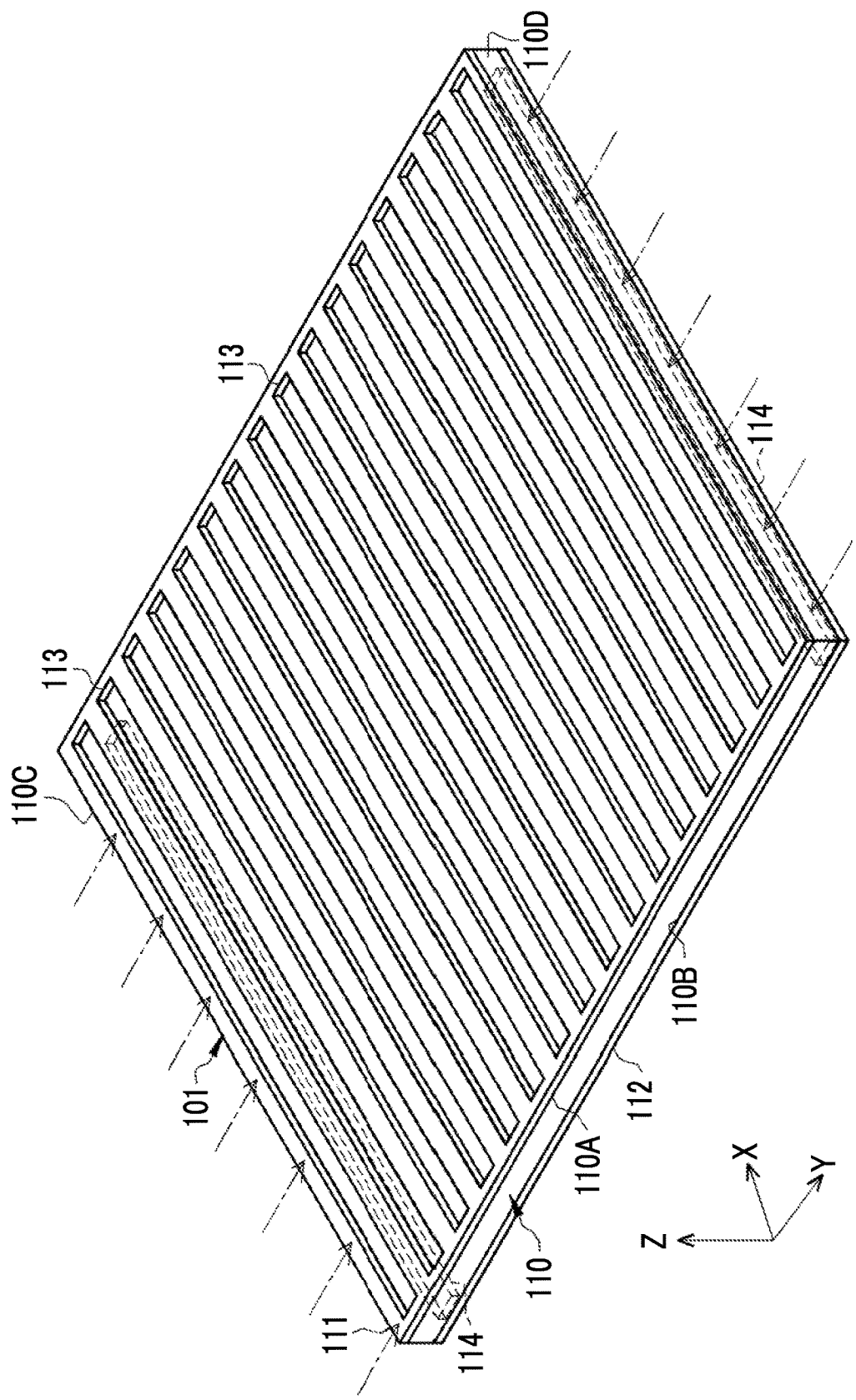
FIG. 20 is a perspective view of a light guide plate as seen from an upper surface side.
Figure 21:
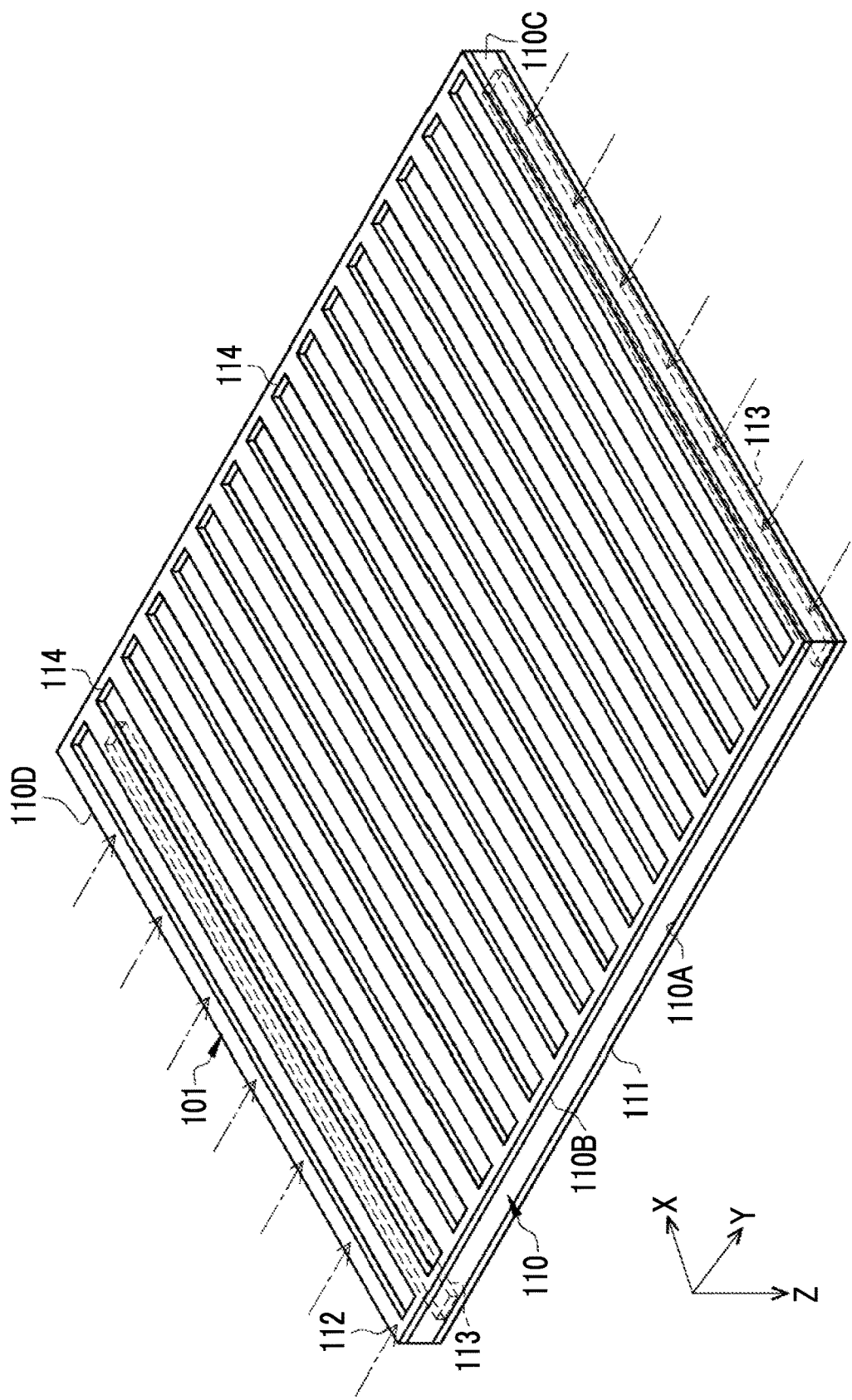
FIG. 21 is a perspective view of the light guide plate as seen from a lower surface side.

As illustrated in FIGS. 20 and 21, the light guide plate 101 has a transmission plate 110, a first reflective film 111, a second reflective film 112, the first openings 113, and second openings 114. Similar to the observation object holding unit 15, the transmission plate 110 is formed of materials, such as glass or resin, which that allows the excitation light and the fluorescence to be transmitted therethrough. The first reflective film 111 and the second reflective film 112 are any one of aluminum films, gold films, silver films, and dielectric multilayer films, and reflect the excitation light. The first reflective film 111 is formed on a surface (hereinafter, an upper surface) 110A of the transmission plate 110 that faces the observation object holding unit 15. The second reflective film 112 is formed on a surface (hereinafter, a lower surface) 110B of the transmission plate 110 that faces the lens unit 72.

The first openings 113 are portions in which the first reflective film 111 is missing in a slit shape on the upper surface 110A of the transmission plate 110. The second openings 114 are portions in which the second reflective film 112 is missing a slit shape at positions that face the first reflective film 111, on the lower surface 110B of the transmission plate 110. For this reason, the first openings 113 and the second openings 114 transmit the excitation light.

The first openings 113 and the second openings 114 are formed at positions corresponding to the lens arrays 25. That is, the width of each first opening 113 in the Y-axis direction is the same as the diameter Φ of the refractive index distribution type lens 26, and the intervals of the adjacent first openings 113 in the Y-axis direction are the same as the width 2W equivalent to the two lens holding parts 71 in the Y-axis direction. The length of the first opening 113 in the X-axis direction is the same as the length of each lens array 25 in the X-axis direction. The same applies to the second openings 114. In addition, in FIG. 20, in order to avoid complication, only two second openings 114 disposed at both ends with respect to the Y-axis direction are drawn. Additionally, in FIG. 21, for the same reason, only two first openings 113 disposed at both ends with respect to the Y-axis direction are drawn.

Figure 22:
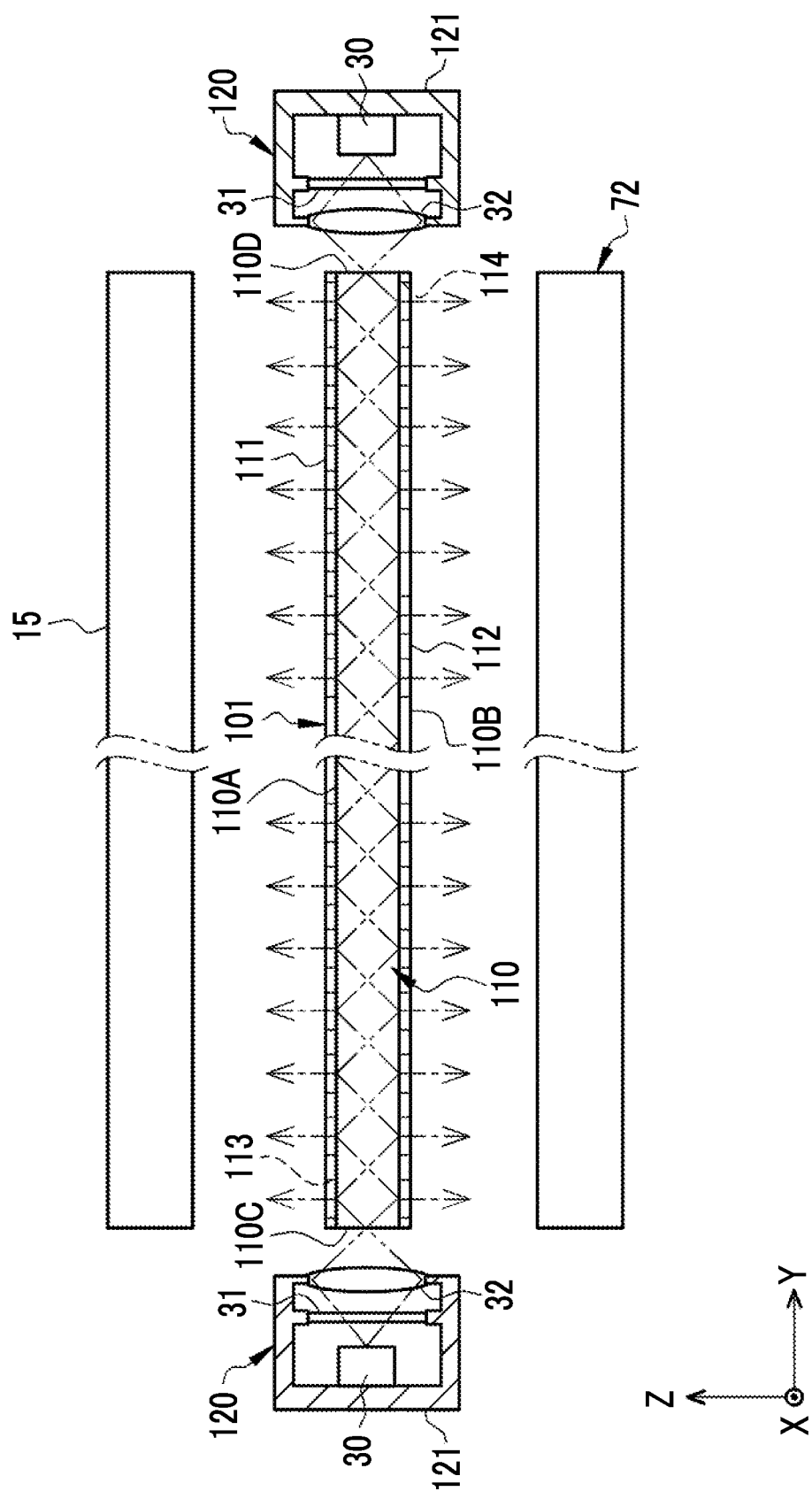
FIG. 22 is a view illustrating the detailed arrangement of the light guide plate and a light source.

In this case, as illustrated by arrows of one-dot chain lines, the excitation light is incident from both side surfaces 110C and 110D on the short side of the transmission plate 110 parallel to the X-axis direction. In more detail, as illustrated in FIG. 22, the excitation light is emitted from light sources 120 disposed at positions that face both the side surfaces 110C and 110D, and is incident on both the side surfaces 110C and 110D. Although only one light source 120 is drawn for each of both the side surfaces 110C and 110D in FIG. 22, a plurality of the light sources 120 are arranged at equal intervals in the X-axis direction in practice. For this reason, as illustrated by one-dot chain lines illustrated in FIGS. 20 and 21, the excitation light is equally incident on both the side surfaces 110C and 110D.

Each light source 120 has the light-emitting element 30, the excitation light transmission filter 31, and the condensing lens 32, similar to the light sources 19 (refer to FIG. 1 and the like) of the first to third embodiments. However, the light source 120 has a configuration that there is no incident end 34 of the optical fiber bundle 20 unlike the light source 19 and the light-emitting element 30, the excitation light transmission filter 31, and the condensing lens 32 are accommodated in a case 121 having a light shielding property. The distances of the light source 120 from both the side surfaces 110C and 110D are adjusted such that the condensing lens 32 is brought into a focus on both the side surfaces 110C and 110D.

As illustrated by arrows of one-dot chain lines, the light guide plate 101 propagates the excitation light, which is incident from the side surfaces 110C and 110D of the transmission plate 110, through the inside of the transmission plate 110 while reflecting the excitation light with the first reflective film 111 and the second reflective film 112, and emits a portion of excitation light, which is propagated through the inside of the transmission plate 110, toward the observation object holding unit 15 (the observation object S is not illustrated) through the first openings 113. Since the first openings 113 are formed in a slit shape that imitates the lens arrays 25, the excitation light is also formed in a slit shape that imitates the lens arrays 25, and is radiated to the observation object holding unit 15. Although the excitation light is also emitted toward the lens unit 72 through the second openings 114, since this excitation light is cut by the excitation light cutoff filter 17 and does not reach the detecting unit 18, there is no influence on the image quality of the fluorescence image.

Additionally, a moving mechanism having the same configuration as the moving mechanism 40 is connected to the light guide plate 101. The light guide plate 101 moves in synchronization with the movement of the lens unit 72 under the control of the movement controller 41 through this moving mechanism. Accordingly, the excitation light is selectively radiated to the position of the observation object holding unit 15 corresponding to the lens arrays 25, and the fluorescence is radiated from the observation object S to which the excitation light is selectively radiated to the detecting unit 18.

The light guide plate 101 is disposed between the observation object holding unit 15 and the lens unit 72. For this reason, constraints for narrowing the distance between the lens unit 72 and the observation object S increase compared to the above first to fourth embodiments in which there is nothing present between the observation object holding unit 15 and the lens unit. However, since the light guide plate 101 has the parallel plate shape and the thickness thereof can be relatively thin as several millimeters, and there are fewer constraints for narrowing the distance between the lens unit 72 and the observation object S than providing the space equivalent to the light source being disposed between the observation object holding unit and the lens unit as in the related art. Hence, the distance between the lens unit 72 and the observation object S can be narrowed to the distance according to the focal length of the refractive index distribution type lens 26, and it is possible to focus the fluorescence emitted from the observation object S on the detecting unit 18 without blurring.

Here, a case where a phosphor sheet including a photostimulable phosphor layer is used as the observation object S is considered. In addition, the phosphor sheet is, for example, a sheet on which a radiographic image of a subject is recorded by receiving radiation transmitted through a subject, such as a patient, and a photostimulable phosphor is excited by radiation of excitation light to emit photostimulable emission light according to the radiographic image. The phosphor sheet is also referred to as an imaging plate.

In a case where the excitation light is radiated to the entire phosphor sheet at once, for example, in a case where the lens unit is at the first position, fluorescence is emitted also from the portion of the phosphor sheet to be detected after the second position. Hence, it is impossible to detect the fluorescence after the second position.

However, according to the light guide plate 101, as mentioned above, the excitation light is selectively radiated to the position of the observation object holding unit 15 corresponding to the lens arrays 25, and the fluorescence is radiated from the observation object S to which the excitation light is selectively radiated to the detecting unit 18. Hence, it is possible to avoid a situation where the excitation light is also radiated at once to portions other than the portion of the phosphor sheet corresponding to the lens arrays 25 and it is impossible to detect the fluorescence of the portion concerned.

Similar to the case of the above fourth embodiment, the light source 19 of each of the above embodiments may be used instead of the light source 120, and the emission ends 36 of the optical fiber sub-bundles 20A may be disposed at both the side surfaces 110C and 110D. In this case, the light guide unit is constituted of the optical fiber bundle 20 (optical fiber sub-bundles 20A) and the light guide plate 101.

In the light guide plate 101 illustrated to FIGS. 20 and 21, the plurality of second openings 114 that are the portions in which the second reflective film 112 are missing are formed in the lower surface 110B of the transmission plate 110. However, as illustrated in FIG. 23, as long as the second reflective film may have the characteristics of reflecting the excitation light transmitting the fluorescence, the second openings 114 may not be provided.

Figure 23:
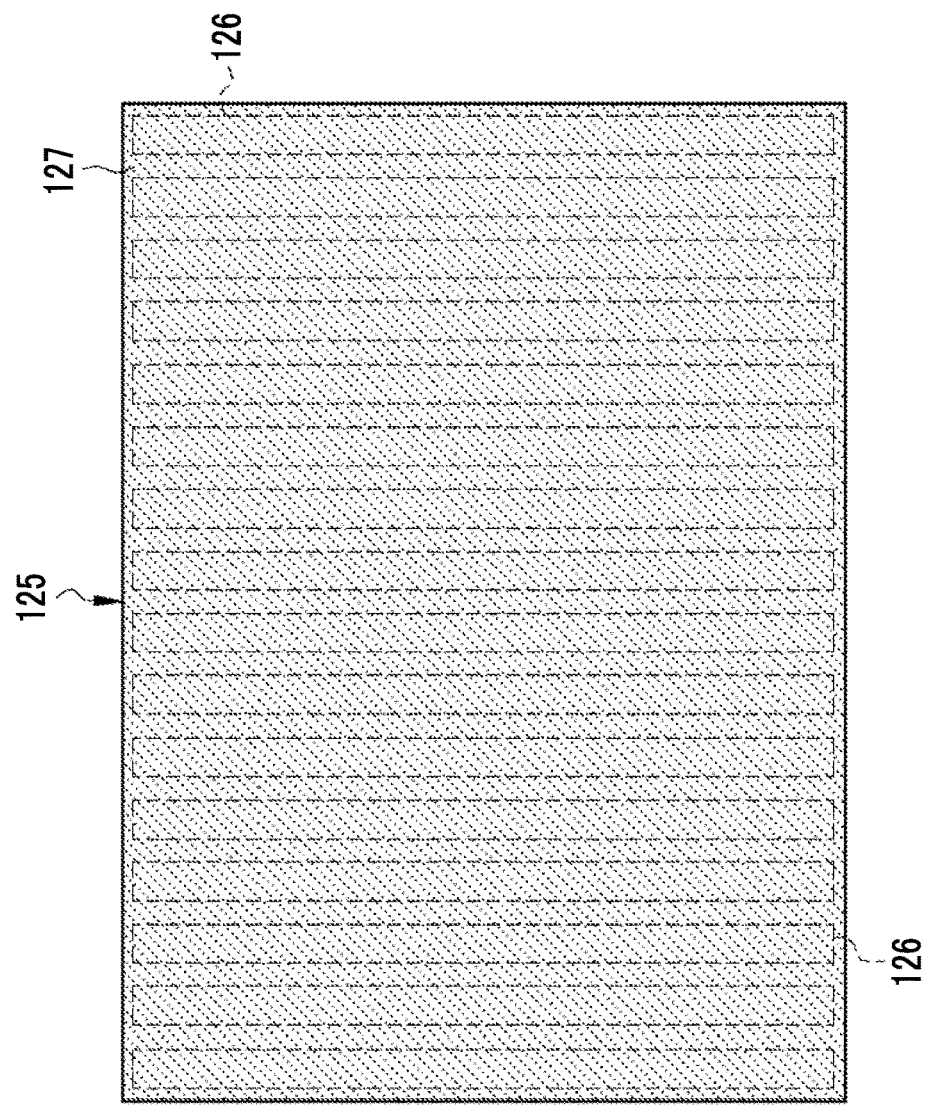
FIG. 23 is a plan view illustrating a light guide plate in which second openings are not formed.

FIG. 23 illustrates a light guide plate 125 as seen from the lower surface side of the transmission plate. In the light guide plate 125, as illustrated by dotted lines, first openings 126 are formed in the upper surface of the transmission plate. However, as illustrated by hatching, the second reflective film 127 is only formed on the whole on the lower surface of the transmission plate, and the second openings are not formed. In this case, the second reflective film 127 is a dielectric multilayer film that reflects the excitation light and transmits the fluorescence.

According to the light guide plate 125 of FIG. 23, since the lower surface of the transmission plate is covered with the second reflective film 127 and does not have the second openings, the excitation light is not emitted toward the lens unit 72 from the second openings 114 unlike the light guide plate 101, and is emitted only from the first openings 126. Since the quantity of the excitation light that does not contribute to fluorescence excitation without being radiated to the observation object S becomes smaller than that in the case of the light guide plate 101, the irradiation efficiency of the excitation light to the observation object S can be raised. Moreover, since the transmission of the excitation light to the lens unit 72 is prevented by the second reflective film 127, that is, the second reflective film 127 plays the role of the excitation light cutoff filter 17, the excitation light cutoff filter 17 can be omitted. Additionally, since the fluorescence is transmitted through the second reflective film 127 and is radiated to the detecting unit 18, there is no influence on the generation of the fluorescence image.

The light guide plate has a configuration in which the excitation light incident from both the side surfaces of the transmission plate is propagated through the inside of the transmission plate and a portion of the excitation light is emitted from the first openings in the middle of the propagation. For this reason, there is concern that the light quantity of the excitation light is lower at the central part of the upper surface of the transmission plate than at the end parts of the upper surface of the transmission plate on both the side surfaces on which the excitation light is incident. Then, it is preferable to make the exclusive area of the first openings at the central part larger than that at the end parts on the upper surface of the transmission plate that faces the observation object S for the purpose of suppressing a decrease in the light quantity of the excitation light at this central part.

Figure 24:
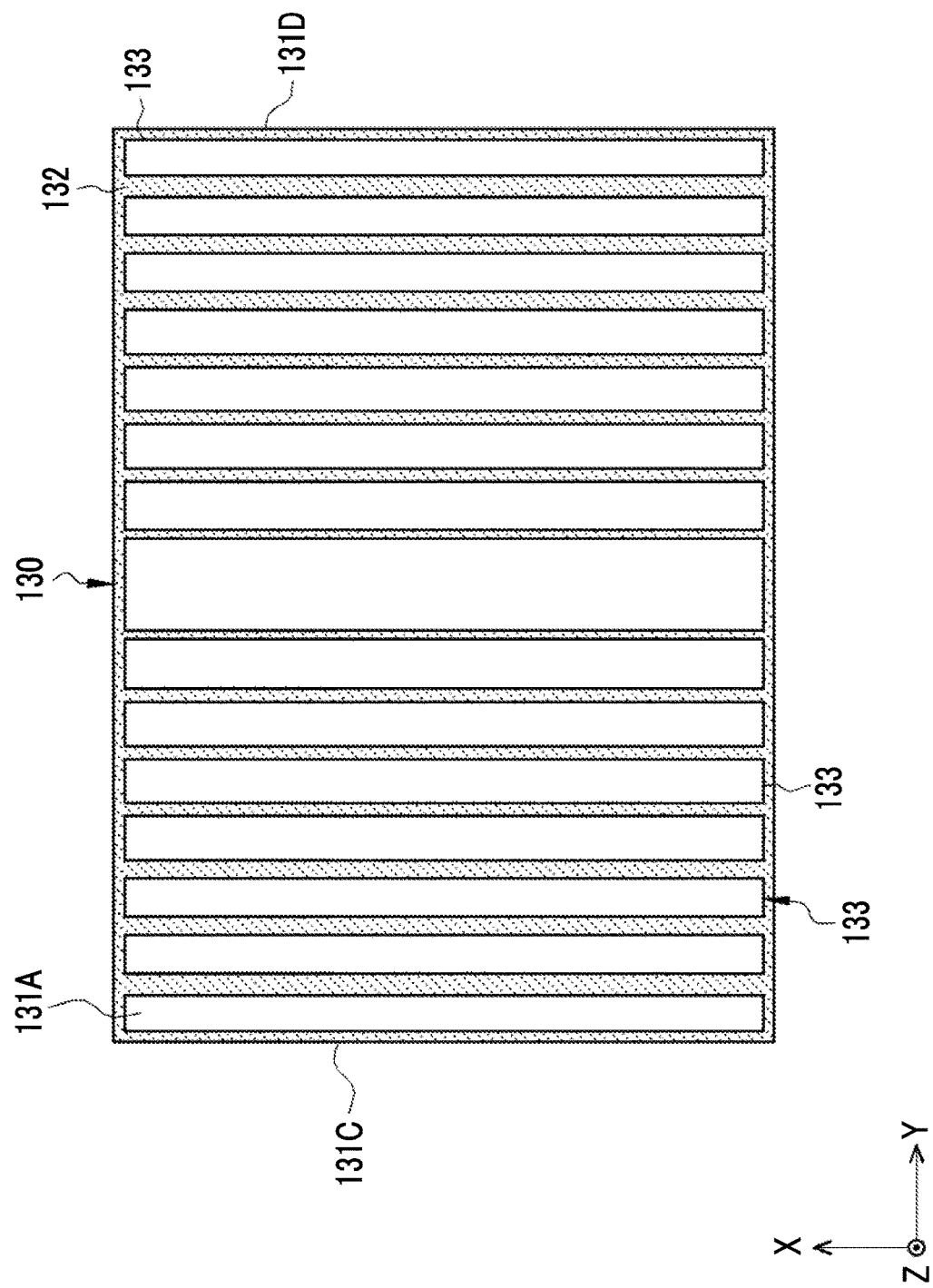
FIG. 24 is a plan view illustrating a light guide plate in which the exclusive area of first openings at a central part is made larger than that at an end part, on an upper surface of a transmission plate that faces an observation object.

In a light guide plate 130 illustrated in FIG. 24, a first reflective film 132 and first openings 133 are formed in an upper surface 131A of a transmission plate. The width of each first opening 133 in the Y-axis direction is the narrowest on both side surfaces 131C and 131D of the transmission plate on which the excitation light is incident. The width gradually becomes wider toward the central part, and becomes the maximum at the central part. That is, in the upper surface 131A of the transmission plate, the exclusive area of the first openings 133 at the central part is large rather than that at the end parts. By adopting this configuration, a decrease in the light quantity of the excitation light at the central part can be suppressed.

The first openings and the second openings may not have the slit shapes. For example, as in a light guide plate 135 illustrated in FIG. 25, in a first reflective film 137 formed on an upper surface 136A of a transmission plate, circularly missing portions that imitate the shape of the refractive index distribution type lens 26 may be used as first openings 138. The first openings 138 are alternately formed in portions corresponding to the refractive index distribution type lenses 26 with respect to the X-axis direction. In addition, in a case where the light guide plate 135 is used, at individual positions, such as a first position, the light guide plate 135 is moved in the X-axis direction by a distance equivalent to the diameter $\Phi$ of each refractive index distribution type lens 26, and the fluorescence before and after the movement is detected by the detecting unit 18.

In the case of the light guide plate 135, simply by making the area of the first openings 138 larger toward the central part, the exclusive area of the first openings 138 at the central part can be made larger than that at the end parts, on the upper surface 136A of the transmission plate. In addition to or instead of this, the number of the first openings 138 may be increased toward the central part.

The above first to third embodiments may be appropriately combined with each other. For example, the above second embodiment and the above third embodiment are implemented in combination, the emission ends 36 of the optical fiber sub-bundles 20A are disposed at the outer periphery of the lens unit 16, and the emission ends 36 are directed to the observation object holding unit 15 and the upper surfaces 76C of the lens holding parts 76. Alternatively, the above first embodiment and the above second embodiment are implemented in combination, the optical fiber sub-bundles 20A may be buried in the lens holding parts 27, the emission ends 36 may be exposed to the upper surfaces 27C of the lens holding parts 27, the emission ends 36 of the optical fiber sub-bundles 20A may be disposed at the outer periphery of the lens unit 16, and the emission ends 36 may be directed to the observation object holding unit 15.

It is needless to say that the invention is not limited to the above first to fifth embodiments and various configurations can be adopted unless departing from the scope of the invention.

EXPLANATION OF REFERENCES 10, 70, 75, 100: fluorescence reading device
15: observation object holding unit
16, 72, 77: lens unit
17: excitation light cutoff filter
18: detecting unit
19, 86, 120: light source
20: optical fiber bundle (light guide unit)
20A: optical fiber sub-bundle (light guide unit)
25: lens array
26: refractive index distribution type lens
27, 71, 76, 85: lens holding part
27A: surface of lens holding part that sandwiches and holds lens array
27B: surface opposite to surface of lens holding part that sandwiches and holds lens array
27C, 76C, 85C: surface (upper surface) of lens holding part that faces observation object holding unit
30: light-emitting element
31: excitation light transmission filter
32: condensing lens
33, 88, 121: case
34: incident end
35: attachment groove
36: emission end
40: moving mechanism
41: movement controller
50: storage unit
51: CPU
52: display unit
53: operating unit
54: operation program
60: light source controller
61: detection controller
62: image generation unit 63: display controller
80: light guide unit
81: first light guide path
81A: opening
82: second light guide path
83: beam splitter (reflecting member)
84: total reflection mirror (reflecting member)
87: collimating lens
90: table
101, 125, 130, 135: light guide plate (light guide unit)
110: transmission plate
110A, 131A, 136A: surface (upper surface) of and the transmission plate that faces observation object holding unit
110B: surface (lower surface) of transmission plate that faces lens unit
110C, 110D, 131C, 131D: side surface of transmission plate on which excitation light is incident
111, 132, 137: first reflective film
112, 127: second reflective film
113, 126, 133, 138: first opening
114: second opening
S: observation object
X: X-axis direction (first direction)
Y: Y-axis direction (second direction)
Z: Z-axis direction
H: distance between lower surface of observation object holding unit and upper surface of lens holding part
Φ: diameter of refractive index distribution type lens
W: width of lens holding part in Y-axis direction
L: center-to-center distance of adjacent lens arrays
ST100 to ST170: step
D: interval of the second light guide path in X-axis direction

What is claimed is:

1. A fluorescence reading device comprising:
an observation object holding unit that holds an observation object that is excited with excitation light to emit fluorescence;
a light source that emits the excitation light;
a detecting unit in which detecting elements for detecting the fluorescence are two-dimensionally arranged;
a lens unit which is disposed between the observation object holding unit and the detecting unit to focus the fluorescence on the detecting unit, and on which a plurality of refractive index distribution type lenses are two-dimensionally arranged;
a moving mechanism configured to move the lens unit; and
a light guide unit that guides the excitation light emitted from the light source to radiate the guided excitation light toward a surface of the observation object that faces the lens unit.

2. The fluorescence reading device according to claim 1, wherein the lens unit is configured such that a plurality of lens arrays in each of which the plurality of refractive index distribution type lenses are arranged in a line in a first direction are arranged in a second direction orthogonal to the first direction,
wherein the lens unit further has a lens holding part, and
wherein the lens holding part includes a pair of parallel flat plates extending in the first direction and sandwiches and holds the lens arrays.

3. The fluorescence reading device according to claim 2, wherein the light guide unit includes an optical fiber that guides the excitation light.

4. The fluorescence reading device according to claim 3,
wherein the light guide unit includes a plurality of the optical fibers,
wherein the optical fibers are buried in the lens holding part, and
wherein emission ends of the optical fibers are exposed to a surface of the lens holding part that faces the observation object holding unit.

5. The fluorescence reading device according to claim 4, wherein the emission ends are equally disposed within the surface of the lens holding part that faces the observation object holding unit.

6. The fluorescence reading device according to claim 4, wherein the emission ends are disposed in a staggered lattice shape within the surface of the lens holding part that faces the observation object holding unit.

7. The fluorescence reading device according to any one of claim 3,
wherein the light guide unit includes a plurality of the optical fibers, and
wherein emission ends of the optical fibers are disposed at an outer periphery of the lens unit.

8. The fluorescence reading device according to claim 7, wherein the emission ends are directed to the observation object holding unit.

9. The fluorescence reading device according to claim 7,
wherein the emission ends are directed to a surface of the lens holding part that faces the observation object holding unit, and
wherein the excitation light reflected by a surface of the lens holding part that faces the observation object holding unit is radiated toward the observation object holding unit.

10. The fluorescence reading device according to claim 9, wherein the surface of the lens holding part that faces the observation object holding unit is used as a scattering surface that scatters the excitation light.

11. The fluorescence reading device according to claim 3, wherein the light source includes
a light-emitting element that emits the excitation light,
an excitation light transmission filter that transmits only light within a preset wavelength range including a central wavelength of the excitation light,
a condensing lens that condenses the excitation light transmitted through the excitation light transmission filter toward an incident end of the optical fiber, and
a light shielding case that accommodates the light-emitting element, the excitation light transmission filter, the condensing lens, and the incident end of the optical fiber.

12. The fluorescence reading device according to claim 2, wherein the light guide unit includes
a first light guide path that is a cavity which is formed within the lens holding part and allows the excitation light to pass therethrough and that extends in the first direction within the lens holding part,
a plurality of second light guide paths that each communicate with the first light guide path are disposed at intervals with respect to the first direction, and each have one end opened toward the observation object holding unit, and
a plurality of reflecting members that are disposed at intersection points between the first light guide path and the plurality of second light guide paths, respectively, and reflect the excitation light passing the first light guide path toward the second light guide paths.

13. The fluorescence reading device according to claim 12,
wherein the reflecting members include beam splitters that transmit a portion of the excitation light and reflect the remainder of the excitation light toward the second light guide paths.

14. The fluorescence reading device according to claim 13,
wherein reflectivities of the beam splitters are adjusted such that light quantities of the excitation light that passes through the plurality of second light guide paths become the same, and the plurality of second light guide paths are equally disposed.

15. The fluorescence reading device according to claim 2,
wherein the light guide unit is a light guide plate having a parallel plate shape that is disposed between the observation object holding unit and the lens unit,
wherein the light guide plate has
a transmission plate that transmits the excitation light and the fluorescence,
a first reflective film that is formed on a surface of the transmission plate that faces the observation object holding unit and reflects the excitation light,
a second reflective film that is formed on a surface of the transmission plate that faces the lens unit and reflects the excitation light, and
a plurality of first openings that are portions in which the first reflective film is missing, in the surface of the transmission plate that faces the observation object holding unit, and
wherein the excitation light incident from a side surface of the transmission plate is propagated through an inside of the transmission plate while being reflected by the first reflective film and the second reflective film, and a portion of the excitation light propagated through the inside of the transmission plate is emitted toward the observation object holding unit through the first openings.

16. The fluorescence reading device according to claim 15,
wherein the light guide plate further has a plurality of the second openings that are portions in which the second reflective film is missing, in the surface of the transmission plate that faces the lens unit.

17. The fluorescence reading devices according to claim 16,
wherein the first reflective film and the second reflective film are aluminum films, gold films, silver films, or dielectric multilayer films.

18. The fluorescence reading device according to claim 15,
wherein the second reflective film is a dielectric multilayer film that reflects the excitation light and transmits the fluorescence.

19. The fluorescence reading device according to claim 15,
wherein an exclusive area of the first openings at a central part is larger than that at an end part, in the surface of the transmission plate that faces the observation object.

20. A fluorescence reading device comprising:
an observation object holding unit that holds an observation object that is excited with excitation light to emit fluorescence;
a light source that emits the excitation light;
a detecting unit in which detecting elements for detecting the fluorescence are two-dimensionally arranged;
a lens unit which is disposed between the observation object holding unit and the detecting unit to focus the fluorescence on the detecting unit, and on which a plurality of refractive index distribution type lenses are two-dimensionally arranged; and
a light guide unit that guides the excitation light emitted from the light source to radiate the guided excitation light toward a surface of the observation object that faces the lens unit, wherein the light guide unit is a light guide plate having a parallel plate shape,
wherein the light guide plate includes:
a transmission plate that transmits the excitation light and the fluorescence;
a first reflective film that is formed on a surface of the transmission plate that faces the observation object holding unit and reflects the excitation light;
a second reflective film that is formed on a surface of the transmission plate that faces the lens unit and reflects the excitation light; and
a plurality of first openings that are portions in which the first reflective film is missing, in the surface of the transmission plate that faces the observation object holding unit, and
wherein the excitation light incident from a side surface of the transmission plate is propagated through an inside of the transmission plate while being reflected by the first reflective film and the second reflective film, and a portion of the excitation light propagated through the inside of the transmission plate is emitted toward the observation object holding unit through the first openings.

21. The fluorescence reading device according to claim 20, wherein the excitation light is incident on a side surface of the light guide plate on which the first reflective film or the second reflective film is not formed.

22. The fluorescence reading device according to claim 21, wherein the excitation light is incident on plural points in the side surface of the light guide plate.

23. The fluorescence reading device according to claim 20, wherein each of the plurality of first openings has a circular shape.

24. The fluorescence reading device according to claim 20, wherein, in the surface of the transmission plate that faces the observation object holding unit, the number of the plurality of first openings at a central part is larger than that at end parts.

* * * * *